United States Patent
Hosemans et al.

(10) Patent No.: US 9,970,023 B2
(45) Date of Patent: *May 15, 2018

(54) **PLANTS OF THE GENUS *DIPLOTAXIS* HAVING CYTOPLASMIC MALE STERILITY**

(71) Applicant: HM.CLAUSE, Portes les Valence (FR)

(72) Inventors: Danièle Hosemans, Angers (FR); Rémi Levieil, Saint Barthélemy d'Anjou (FR)

(73) Assignee: HM. CLAUSE, Portes Les Valence (FR)

( * ) Notice: Subject to any disclaimer, the term of this patent is extended or adjusted under 35 U.S.C. 154(b) by 134 days.

This patent is subject to a terminal disclaimer.

(21) Appl. No.: 14/844,618

(22) Filed: Sep. 3, 2015

(65) Prior Publication Data

US 2015/0368664 A1 Dec. 24, 2015

Related U.S. Application Data

(63) Continuation of application No. 13/203,953, filed as application No. PCT/FR2010/000182 on Mar. 2, 2010, now Pat. No. 9,133,476.

(30) Foreign Application Priority Data

Mar. 2, 2009 (FR) ..................... 09 00930
Apr. 9, 2009 (FR) ..................... 09 01763

(51) Int. Cl.
*A01H 1/02* (2006.01)
*A01H 5/12* (2018.01)
*C12N 15/82* (2006.01)
*C07K 14/415* (2006.01)

(52) U.S. Cl.
CPC ........... *C12N 15/8289* (2013.01); *A01H 1/02* (2013.01); *A01H 5/12* (2013.01); *C07K 14/415* (2013.01)

(58) Field of Classification Search
None
See application file for complete search history.

(56) References Cited

U.S. PATENT DOCUMENTS 8,044,267 B2 * 10/2011 Olesen ............... A01H 1/00 435/430.1

FOREIGN PATENT DOCUMENTS

| EP | 2 111 748 A1 | 10/2009 |
| FR | 2 667 078 A1 | 3/1992 |
| WO | WO 2008/084329 A3 | 7/2008 |

OTHER PUBLICATIONS

Klimaszewska et al. Plant Science 58: 211-222 (1988).*
Duroc et al. Biochimie 87: 1089-1100 (2005).*
Eschmann-Grupe et al. Plant Systematics and Evolution 243: 13-29 (2003).*
Bang et al. (2003). Production of intergeneric hybrids between the $C_3$—$C_4$ intermediate species *Diplotaxis tenuifolia* (L.) DC. and *Raphanus sativus* L. Breeding Science, 53, 231-236.
Pellan-Delourme & Renard (1987). Identification of maintainer genes in *Brassica napus* L. for the male-sterility-inducing cytoplasm of *Diplotaxis muralis* L. Plant Breeding, 99, 89-97.
Flannery et al. (2006) Plastid genome characterisation in *Brassica* and Brassicaceae using a new set of nine SSRs. Theor Appl Genet, 113, 1221-1231.
Cao & Earle (2003). Transgene expression in broccoli (*Brassica oleracea* var. *italica*) clones propagated in vitro via leaf explants. Plant Cell Rep, 21, 789-796.
Matsuzawa et al. (1999). Male sterility in alloplasmic *Brassica rapa* L. carrying *Eruca sativa* cytoplasm. Plant Breeding, 118, 82-84.
Rahman (2004). Optimum age of siliques for rescue of hybrid embryos from crosses between *Brassica oleracea*, *B. rapa* and *B. carinata*, Canadian Journal of Plant Science, 84(4), 965-969.
International Search Report, dated Apr. 29, 2010 by the International Searching Authority (ISA/EP) in connection with PCT International Application No. PCT/FR2010, 000182, filed Mar. 2, 2010.
Written Opinion of the International Searching Authority, dated Apr. 29, 2010 by the International Searching Authority (ISA/EP) in connection with PCT International Application No. PCT/FR2010, 000182, filed Mar. 2, 2010.

* cited by examiner

*Primary Examiner* — David T Fox
(74) *Attorney, Agent, or Firm* — John P. White; Cooper & Dunham, LLP

(57) ABSTRACT

The present invention concerns plants, seeds and cells of the genus *Diplotaxis* having cytoplasmic male sterility, and more particularly plants, seeds and cells of the species *Diplotaxis tenuifolia*. The cytoplasmic male sterility is preferably that imported from *Raphanus sativus*, known as Ogura sterility. The invention also concerns methods for obtaining *Diplotaxis tenuifolia* plants carrying cytoplasmic male sterility, as well as various uses for the cytoplasmic male sterility of the plants of the invention.

16 Claims, 2 Drawing Sheets

Figure 2:
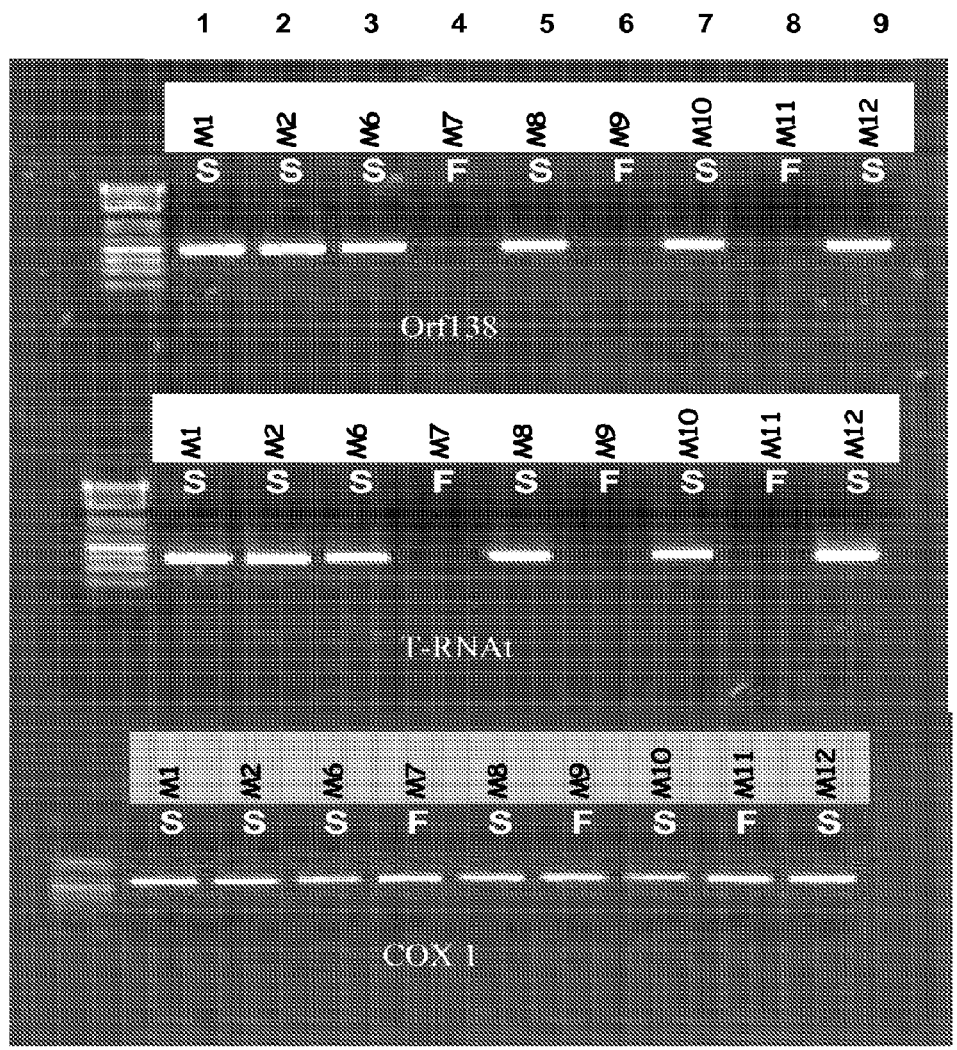

```
   1 aagcttgaag ggtaatatct tcgccaccct cccgactcgc aatccccaat gtggctttcc
  61 tcacttcggt aagttacaag gatgaatgca aatagcaagg cgctatgctg cgtgaagtga
 121 gaccggctgt cctaagttaa gttgcttcct tattcattaa tgatcttgct cagtaggagg
 181 gcttttcccc ttctgtgcag cctgatttta tctctggaaa tgagggtgcc ctcgattgca
 241 attttttcatc gaatatgatg gattcccccc atggtgagaa ggttgagtta cagactccgt
 301 tggctttcgc aagacagtct cgaaagttcc gaaatctatg gttgatgtct cactcgaact
 361 ctatccctga cttcttcgt ccgagcggcc cctctaggag ccgatgcggg aaggaagaag
 421 gatttatttc taccattaaa taattcgcaa tagttaacca agcagtagcc aagaacaaag
 481 aagcaagcca agatcaatgg gggggtcgc cccagtcaaa aatggtaaga aggagtagca
 541 tcaataacat tcattgtatg tacgcctccc agcgatccac aggcatctgt agcatgttgt
 601 acccgagagt tattttggct gtgtctgtta caccatggac aataatctta gtcggagtca
 661 aattccttac ctttccaccc aaagctgaac atatccgcac agatattcca tttttttat
 721 tgaggatcca ttttcgaact gaactactca tgcttaggca aaacaagcaa gggagttgtt
 781 aataaggagc tagctacagt gctcctgcgg gagggttccc gtgcttatta aggagccggg
 841 cagctacgca acacttcctt gcaactcata cctactaaca aactgtttac tcttttttaag
 901 gagttagctg catttccctg cggaggtacg tacgcaatca aagcagcagg gcagcttcgc
 961 aacacctgct tcaacttcat gcacattagc aacaagattg ggtagttgat tgttgggagg
1021 atagctgcag ctccctacgg gagtgaacta cagttccagg gggagcacag caagggccaa
1081 taccggctgt gaggcgcgta gcgggaagag atgtatggta agggatagct gtttaaccat
1141 ttgtaatgga atgggatgtt gatcctcctt ggaataatac gtatataaga agattttcat
1201 tccagttgga aagcaatcga gaaaacgccg cccaaatacg gttcgccacg tgtagccctg
1261 tatggactcg cgaagcaggt ctccggtcgg tgtccaagat ttgatctaac tattgagtga
1321 ggactactta ccgattgata gaataatacg tatataagaa gaaggctgct ttgtggagtg
1381 atctttctcg aaatgaatta agtaagggcg ctatgttcag attctgaacc aaagcactag
1441 ttgaggtctg aaagccttat gagcagaagt aataaataco tcgggggaaga agcggggtag
1501 aggaattggt caactcatca ggctcatgac ctgaagatta caggttcaaa tcctgtcccc
1561 gcaccgtagt ttcattctgc atcactctcc ctgtcgttat cgacctcgca aggttttga
1621 aacggccgaa acgggaagtg acaataccgc ttttcttcag catataaatg caatgattac
1681 ctttttcgaa aaattgtcca cttttttgtca taatctcact cctactgaat gtaaagttag
1741 tgtaataagt ttctttcttt tagctttttt actaatggcc catatttggc taagctggtt
1801 ttctaacaac caacattgtt tacgaaccat gagacatcta gagaagttaa aaattccata
1861 tgaatttcag tatgggtggc taggtgtcaa aattacaata aaatcaaatg tacctaacga
1921 tgaagtgacg aaaaaagtct cacctatcat taaaggggaa atagagggga aagaggaaaa
1981 aaaagagggg aaggggaaa tagaggggaa agaggaaaaa aaagagggga aagggaaat
2041 agagggaaa gaggaaaaaa aagaggtgga aaatggaccg agaaaataat gctttgtgaa
2101 cccaattgct ttgacaaataa taaagaaaga agcaaaatct cattcaattt gaaatagaag
2161 agatctctat gccccctgtt cttggttttc tcccatgctt ttgttggtca acaaccaacc
2221 acaacttct atagttcttc actactccta gaggctttgg taatgaagct gtctggaggg
2281 atttgttgaa atcaattaat ctaatcatgc ctcaactgga taaattcact tattttcac
2341 aattcttctg gttatgcctt ttcttcttta cttctatat tttcatatgc aatgatggag
2401 atggagtact tgggatcagc agaattctaa aactacggaa ccaactgctt tcacaccggg
2461 ggaagaccat ccagagcaag gaccccaaca gtttggaaga tctcttgaga aaaggtttta
2521 gcactggtgt atcctatatg tatgctagtt tattcgaagt atcccaatgg tgtaaggccg
2581 tcgacttatt gggaaaaagg aggaaaatca ctttgatctc ttgtttcgga gaaataagtg
2641 gctcacgagg aatggaaaga aacatattat ataatctatc gaagtcctct ccttcaaata
2701 ctggaaggtg gatcacttgt aggaattgta ggaatgacat aatgctaatc catgctgtac
2761 atggccaagg aagcataaaa tgattctttc attctataga tacctctggt aggtaaagca
2821 ctctactgtg ctttattgaa agttcccatc gcggggcag ggatacttgc cttcgcggtt
2881 cgactttctt ttcaggcttg actcattatt ttccggtcct ctcacacccc tttagagctc
2941 tttatgatgc ccactgagta agattcgggg gcttaccggc gcagaagctc attctgaacc
3001 gcgggaacct tcgtctcttc gacacaaacg ttttatgaag aggctgatgg tgatgaggat
3061 ccatgcgcac tcaaataaaa gtagcttgcg tattggtta tccacggtgt taggtgctcc
3121 attgcacctc atgtggaggt aggataattt ggactcttt ggagcactat actccgaaag
3181 atcctatcct tcctcctctt ctttcagtcg agacttcctc ctagtgaggt gttgcctatc
3241 caggtatgga agtattcaat gaatacactc tgtaccatgg gtggatgaag ctt
```

Z18896 SEQ ID N°1

FIGURE 1

PLANTS OF THE GENUS *DIPLOTAXIS* HAVING CYTOPLASMIC MALE STERILITY

This application is a continuation of U.S. Ser. No. 13/203,953, filed Jan. 13, 2012, now U.S. Pat. No. 9,133,476, issued Sep. 15, 2015, which is a § 371 national stage of PCT International Application No. PCT/FR2010/000182, filed Mar. 2, 2010, which claims priority of French Patent Applications Nos. 0901763, filed Apr. 9, 2009 and 0900930, filed Mar. 2, 2009, the entire contents of each of which are hereby incorporated by reference into this application.

This application incorporates-by-reference nucleotide and/or amino acid sequences which are present in the file named "150903_0857_83252-A_Substitute_Sequence_Listing_AHC.txt", which is 10.4 kilobytes in size, and which was created Sep. 3, 2015 in the IBM-PC machine format, having an operating system compatibility with MS-Windows, which is contained in the text file filed Sep. 3, 2015 as part of this application.

The present invention relates to plants of the genus *Diplotaxis*, and more particularly of the species *Diplotaxis tenuifolia*, carrying cytoplasmic male sterility, to seeds and cells deriving from or giving rise to said plants, and to a method for producing them.

Plants of the species *Diplotaxis tenuifolia* are known by the generic term "rocket" salad (rucola, arugula). However, in reality the term rocket salad represents two different genuses, *Eruca* and *Diplotaxis*; all they have in common is that they belong to the same family, Brassicaceae (formerly known as Crucifers). "Cultivated" rocket salad is *Eruca sativa* L. and the "wild" rocket salad is *Diplotaxis tenuifolia* L.

Rocket salad has been consumed for many years in Europe, but the species known as the wild species has not been cultivated but simply harvested from nature, whence the terms "wild" and "cultivated", deriving from the old production techniques.

More particularly, the present invention concerns the rocket salad known as "wild", *Diplotaxis tenuifolia*. It is a leaf vegetable consumed as salad, occasionally as a mixture as in the traditional Mesclun, providing a more spicy, less bitter note than cultivated rocket.

The recent development of the industrial culture of lamb's lettuce, principally in the Nantes region, due to the introduction of ready-to-eat fresh produce lines, has led to the development of the production of "baby" salads, then to the production of rocket. The culture of rocket salad known as "wild rocket" has thus grown in leaps and bounds in the last few years in Europe where it is preferred to "cultivated" rocket, especially in Germany and Italy where its development has been very rapid.

Due to the change in the production of rocket, especially of the species *Diplotaxis tenuifolia*, improving these plants has become a major objective for producers and seed manufacturers.

Since plants of the genus *Diplotaxis*, and especially of the species *Diplotaxis tenuifolia*, are preferably allogamous, the best solution to bringing about substantial improvements for the benefit of the producers consists of creating varieties known as "F1 hybrids". Hybrid plants in fact have better homogeneity characteristics in the field, so that in particular a uniform harvest can be obtained, and they are also more vigorous than open pollinated varieties. Further, hybrid production allows for varietal improvement, qualitative improvements (leaf shape, plant habit, leaf color, flavor, etc) and rises in yield due to better productivity. They can also be used to introduce and accumulate resistance to certain pathogens or predators which affect the culture, as well as tolerances to abiotic stresses.

However, such "F1" plants do not exist in *Diplotaxis tenuifolia* and are not mentioned in the literature.

The production of F1 hybrid plants can indeed only be envisaged economically if there is the possibility of producing commercial seeds at reasonable cost. Thus, manual pollination (an operator removes pollen from the male parent and deposits it on the reproductive organs of the female parent, while ensuring that the female is not self-pollinated) is immediately excluded, along with emasculation of flowers (necessary to ensure the absence of self-pollination).

Entomophilous pollination is not directed, and so a biological system has to be available to force cross pollination between parental lines. Further, it also has to involve the prior manual emasculation of flowers, which is incompatible with industrial production.

Thus, the present inventors sought to provide the culture of rocket with improvements by producing plants of the genus *Diplotaxis* with cytoplasmic male sterility, and F1 hybrid plants.

Two categories of natural systems exist which can be used in Brassicaceae to obtain hybrid plants, namely auto-incompatibility and male sterility.

The first (auto-incompatibility) is well known in Brassicaceae; however, it has certain limitations in use; in Brassicas, auto-incompatibility has been used for a long time; however, that phenomenon is not reliable and batches of the seeds produced are often mixtures of F1 seeds and seeds derived from self-fertilization.

The second is based on the absence of viable pollen (male sterility) on one of the parental lines, which means that 100% hybrid seed batches can be obtained.

That sterility may be of two types, genetic or cytoplasmic. Genetic sterility, recessive or dominant, is occasionally used, but it is a difficult technique to use. Further, genetic male sterility is unknown in *Diplotaxis*.

The present inventors thus conceived the idea of using cytoplasmic male sterility to produce F1 hybrids. That technique has been used to produce F1 hybrids, in particular in radishes, carrots, celery, beetroot, onions, sunflower, fennel, etc.

However, for the genus *Diplotaxis*, and in particular for *Diplotaxis tenuifolia*, no cytoplasmic male sterility has been observed in existing cultivars or in wild populations, in contrast to the plants cited above.

Another possibility is to import cytoplasmic male sterility originating from "related" species into the genus *Diplotaxis*.

However, according to the literature, there are no species of the genus *Diplotaxis* that are carriers of a well-characterized cytoplasmic male sterility which could be suitable for importing into other species of the genus *Diplotaxis*.

Thus, the inventors used cytoplasmic sterility originating from plants of a "related" genus and not from a related species, in this case originating from plants of the genus *Raphanus* (species *Raphanus sativus*), by crossing using original protocols.

This approach is highly inventive as it involves intergeneric crosses (i.e. between plants of different genuses and not solely of different species) and it is well known to the skilled person that such crosses are rarely viable, especially when the number of chromosomes is different, which is the case with the present invention: *Raphanus sativus* has 2n=18 chromosomes and *Diplotaxis tenuifolia* has 2n=22 chromosomes.

Further, such crosses, when they are viable, are even more rarely fertile. The inventors have in fact demonstrated that an intergeneric cross between plants of the species *Brassica rapa* with cytoplasmic male sterility and plants of the species *Diplotaxis tenuifolia* did not lead to the production of descendants and that the same is true for an intergeneric cross between *Brassica oleracea* plants carrying cytoplasmic male sterility and *Diplotaxis tenuifolia* plants.

Further, this approach involves cohabitation, in the same cell, of chloroplastic and nuclear genomes originating from different genuses. In fact, the chloroplastic genome derives from the genus known as "related" which provides the cytoplasmic male sterility as the female parent, namely the genus *Raphanus* (*Raphanus sativus*), while the nuclear genome is from the genus *Diplotaxis*. However, in crucifers (Brassicaceae), patent EP 0 549 726 teaches that combining nuclear and chloroplastic genomes of different genuses in the same cell leads to the phenomenon of chlorosis. Such a phenomenon of chlorosis is entirely incompatible with the aim of commercialization for consumption.

In their 2003 publication, Bang S W et al described crossing a plant of the species *Diplotaxis tenuifolia* (female parent) and a plant of the species *Raphanus sativus* (male parent) by embryo rescue and amphidiploid induction, followed by various crosses with *Diplotaxis tenuifolia* or *Raphanus sativus* plants. No mention of cytoplasmic male sterility was made in that article.

Further, it should also be noted that the authors of the article indicated that embryos could not be obtained from an intergeneric cross in which *Raphanus sativus* was the female parent and *Diplotaxis tenuifolia* was the male parent; thus, they considered that cross to be an incompatible cross.

The present invention concerns male sterile plants of the genus *Diplotaxis*, especially of the species *Diplotaxis tenuifolia*, due to cytoplasmic male sterility, their various constituents in particular cells, seeds derived or originating from said plants, and methods for obtaining them.

In the context of the present invention, the following terms have the particular meanings given below:

Backcross denotes crossing a hybrid with one of the two (2) parental types that have been used to form it.

Percentage identity of two sequences: the degree or percentage of identity between two sequences (proteic or nucleic) is determined by aligning the two sequences in order to maximize the points that are in agreement while minimizing the gaps; it is obtained by dividing the number of common amino acids or nucleic acids by the longest length of the two sequences.

The present invention is directed to a plant of the genus *Diplotaxis*, characterized in that it carries cytoplasmic male sterility.

*Diplotaxis* is a genus of diploid plants with flowers, from the Brassicaceae family, originating from the Mediterranean basin.

The term "male sterility" for an allogamous plant means that said plant cannot be a male parent during a cross, but possibly a female parent. Although reference may occasionally be made to a "male" or "female" plant, it should be noted that this terminology is incorrect; in the case of male sterility, it is in fact a hermaphrodite flower which has deficient (or inoperative) male organs and which thus can only be used as a female flower.

In accordance with the present invention, male sterility is preferably characterized by the absence of viable pollen that could fertilize female organs (deficient male organs). A male sterile plant therefore could not participate in crossing as the male parent.

A male sterile plant of the present invention is preferably completely female fertile, i.e. it can participate in a cross as the female parent with the same degree of fertilization as a plant that was male fertile.

Cytoplasmic male sterility is a male sterility carried by the cytoplasm of the plant or cell, and more particularly encoded by its mitochondrial genome. Since the cytoplasm (and thus the mitochondrial genome) is inherited from the female parent, any plant from a cross between a plant of the invention as the female parent (i.e. with cytoplasmic male sterility) and a male parent of any type will also carry the cytoplasmic male sterility (or CMS, cytoplasmic male sterility) of the female parent. Since a plant of the invention cannot be a male parent in a cross because of its male sterility, any plant derived from crossing a plant of the invention is also a carrier of cytoplasmic male sterility. Thus, it is a trait that will necessarily be inherited by all of the descendants of a plant or seed of the invention.

The cytoplasmic male sterility of the invention is a stable, reliable sterility, i.e. all of the descendants of a plant of the invention are male sterile.

Preferably, the invention concerns a plant of the species *Diplotaxis tenuifolia*, which is the most widespread species of the genus *Diplotaxis*. It is a salad plant with a piquant, slightly bitter flavor, usually known as "wild rocket". A plant of the species *Diplotaxis tenuifolia* is diploid, with $2n=22$.

A plant of the invention preferably has a perfectly normal phenotype, i.e. a phenotype essentially identical to that of a male fertile plant of the same species, the only difference being the male sterile or fertile character. For breeders, it is important that there is no statistically significant detectable difference in phenotype, in particular in shape, size, color or leaf flavor. Moreover, the absence of difference in ploidy is also required.

In particular, a plant of the present invention displays no symptoms of chlorosis under normal culture conditions, especially when the temperature is below 10° C., for example when the temperature is in the range 5° C. to 10° C. The term "chlorosis" means a more or less pronounced discoloration of the leaves due to a lack of chlorophyll.

Having regard to commercialization for consumption, it is thus important that a plant of the invention should not be affected by chlorosis at any stage of development of the plant under normal culture conditions, especially when the temperatures are reduced.

The term "normal culture conditions" means culture conditions that do not induce any symptoms of chlorosis in an ordinary plant of the species *Diplotaxis tenuifolia* (male and female fertile).

In accordance with a preferred embodiment of the invention, the plant of the invention with cytoplasmic male sterility is homozygous over all of its genome (nuclear) or at least by more than 90% or even more than 95% or more than 99%.

In accordance with another preferred embodiment of the invention, the plant in question is a hybrid F1 plant. It preferably derives from crossing two plants of the same species, preferably *Diplotaxis tenuifolia*, which originate from two phenotypically different lines.

Whatever the case, the female parent of a F1 hybrid plant of the invention is a plant of the genus *Diplotaxis*, preferably of the species *Diplotaxis tenuifolia*, carrying cytoplasmic male sterility.

Cytoplasmic male sterility is known in the natural state in the species *Raphanus sativus* (radish) and this male sterility has already been exploited under the name Ogura cytoplasmic male sterility. It has in particular been transmitted to various species of the genus *Brassica*, as demonstrated in patent EP 0 549 726. It is thus characterized by the DNA sequence included between nucleotides 928 and 2273 of FIG. 1 of patent EP 0 549 726 or a sequence having at least 50% identity with said sequence and providing cytoplasmic male sterility when it is present in the mitochondrial genome of a plant.

Preferably, the cytoplasmic male sterility of the present invention is a sterility derived from the cytoplasmic male sterility of *Raphanus sativus*, which results in the presence in the mitochondrial genome of a plant of the invention of sequences originating from *Raphanus sativus*, preferably originating from the mitochondrial genome of *Raphanus sativus*. Said sequences originating from the mitochondrial genome of *Raphanus sativus* preferably represent at least 50% of the mitochondrial genome according to the invention or have a length of at least 50, or even at least 100, 200, 500 or 1000 consecutive base pairs.

In a preferred embodiment, the mitochondrial genome of a plant of the invention comprises at least a portion of the DNA sequence illustrated in FIG. 1 (SEQ ID No 1 corresponding to Z18896, which comprises the orf138 gene of Ogura male sterile *R. sativus*), this portion comprising at least 50 consecutive base pairs of SEQ ID No 1. Preferably, said portion of SEQ ID No 1 has a length of at least 100, preferably at least 200, 500, 1000 or 2000 base pairs.

In another preferred embodiment, the mitochondrial genome of a plant of the invention comprises at least one sequence having at least 50% identity with a portion of the DNA sequence illustrated in FIG. 1 (SEQ ID No 1), this portion comprising at least 50 consecutive base pairs of SEQ ID No 1, preferably at least 100, preferably at least 200, 500, 1000 or 2000 base pairs. Preferably again, said sequence has at least 70%, preferably at least 80% identity, or even at least 90% or 95% identity or even at least 99% identity with said portion of SEQ ID No 1.

Particularly preferably, the portion of SEQ ID No 1 present in the genome of a plant of the invention provides cytoplasmic male sterility.

Preferably, said portion corresponds to nucleotides 1673 to 2089 of SEQ ID No 1, which include orf138. This sequence is in fact characteristic of the cytoplasmic male sterility known as Ogura. Alternatively, said portion is a 512 base pair fragment corresponding to nucleotides 1579 to 2090 of SEQ ID No 1 including the orf138 gene, or a 401 base pair fragment corresponding to nucleotides 1248 to 1648 of SEQ ID No 1, comprising all or a portion of the T-RNAt gene (Transfer-RNAt formylmethionine).

For this reason, a plant of the invention is preferably characterized by an amplified fragment with the following size when the corresponding primers are used to amplify the mitochondrial genome of the plant by PCR:
  512 base pairs when the oligo primers 37 and 38 (SEQ ID No 22 and 23 respectively) are used; and/or
  401 base pairs when the primers TRNAFM-610U and TRNAFM-987L (SEQ ID No 24 and 25 respectively) are used.

Preferably, the sequence for the amplified fragment of 512 base pairs is SEQ ID No 20 and this sequence is present in the genome of a plant of the invention.

Preferably, the sequence for the amplified fragment of 401 base pairs is SEQ ID No 21 and this sequence is present in the genome of a plant of the invention.

Furthermore, in a preferred implementation of the present invention, a plant as described carrying cytoplasmic male sterility is also distinguished in the chloroplastic genome from another plant which does not carry said sterility.

Preferably, a plant of the invention comprises in its chloroplasts, in the chloroplastic DNA, sequences which are not from the genus *Diplotaxis*. As an example, at least 50 base pairs of the chloroplastic genome are not from the genus *Diplotaxis*, preferably at least 100, 200, 500 or even a thousand bases. Preferably, the entire chloroplastic genome is not that of the genus *Diplotaxis*.

The portion of the chloroplastic genome which is not of the genus *Diplotaxis* is preferably of the species *R. sativus*. Preferably, it is all or a portion of the chloroplastic genome of *Raphanus sativus*. As described above, said sequences contain DNA sequences comprising at least 50, or even at least 100, 200 or at least 500 consecutive base pairs. Preferably, the chloroplastic genome of a plant of the invention derives of the species *Raphanus sativus*, and so it contains no sequences characteristic of the chloroplastic genome of *B. rapa* or *B. oleracea*, or any other *Brassica*.

In accordance with an embodiment illustrated in more detail in the experimental portion of this application, a plant in accordance with the invention is characterized by cells that have the genomic DNA of *Diplotaxis tenuifolia*, the mitochondrial DNA of Ogura *Raphanus sativus* sterility and the chloroplastic DNA of *Raphanus sativus*.

Protocols allowing sequences within the mitochondrial and chloroplastic genome of a plant cell to be determined are described in the experimental section (see Example 2 for the chloroplastic genome and the mitochondrial genome). They can be carried out to determine whether a given plant, which is cytoplasmic male sterile, comprises sterility known as Ogura in its mitochondrial DNA and comprises chloroplastic DNA of *Raphanus sativus*.

A plant of the invention is preferably characterized by an amplified fragment with the following size when the corresponding primers are used to amplify the chloroplastic genome of the plant by PCR:
  193 base pairs when the oligo primers MF2_M13F and MF2_R (SEQ ID No 4 and 5 respectively) are used; and/or
  264 base pairs when the primers MF8_M13F and MF8_R (SEQ ID No 16 and 17 respectively) are used; and/or
  180 base pairs when the primers MF7_M13F and MF7_R (SEQ ID No 14 and 15 respectively) are used; and/or
  319 base pairs when the primers MF9_M13F and MF9_R (SEQ ID No 18 and 19 respectively) are used; and/or
  303 base pairs when the primers MF3_M13F and MF3_R (SEQ ID No 6 and 7 respectively) are used; and/or
  183 base pairs when the primers MF6_M13F and MF6_R (SEQ ID No 12 and 13 respectively) are used.

Said primers hybridize with the chloroplastic genomes of the plants *D. tenuifolia*, *R. sativus* CMS and *B. oleracea* Ogura CMS, but the size of the amplified fragment varies and characterizes the plants in accordance with the invention, for which the cytoplasm derives from *R. sativus* CMS, as will become apparent from example 2.

In order to determine whether a sterile male plant carries cytoplasmic or genomic sterility, a simple test protocol consists of carrying out crosses with a fertile plant and determining the proportion of the descendants which is also male sterile. In the case of cytoplasmic male sterility, any plant from said cross is also male sterile, as well as any plant derived from this crossing by backcrossing with the fertile plant.

In the case of a recessive genomic sterility, in general no plant derived from this cross is male sterile.

In the case of dominant genomic sterility, half of the plants derived from this cross are also male sterile. If the genomic sterility is dominant, the female parent can only be heterozygous for this sterility gene and thus only transmits this trait to half of its descendants. Thus, the segregation is Mendelian in nature in the descendants in the case of genomic sterility, while there is no segregation in the case of cytoplasmic sterility since the heredity is female.

It should be noted that the distinction between a male sterile plant (cytoplasmic) of the invention and a male fertile plant may be made with the naked eye; the plants are phenotypically different due to the absence of pollen in the case of male sterile plants.

The plant of the genus *Diplotaxis* of the present invention are preferably obtained without having recourse to protoplast fusion and without inducing doubling of the number of chromosomes at any stage of production in order to preserve diploidy.

The present invention also concerns seeds of the genus *Diplotaxis*, more particularly of the species *Diplotaxis tenuifolia*, and more particularly seeds carrying cytoplasmic male sterility. The invention in particular concerns seeds that, after germination, can produce a plant as described above, i.e. of the genus *Diplotaxis* and carrying cytoplasmic male sterility, more particularly of the species *Diplotaxis tenuifolia*. It also concerns seeds derived from crossing a plant as described above with another plant of the species *Diplotaxis tenuifolia* which is male fertile. As indicated above, any seed derived from crossing a plant of the invention and another plant of the species *Diplotaxis tenuifolia* will also give rise to a plant of the species *Diplotaxis tenuifolia* with cytoplasmic male sterility.

We have already specified above what is understood by the term "cytoplasmic male sterility" in the context of the plants of the invention; for the seeds of the invention, the definitions and preferred embodiments are the same.

It should be noted that the cytoplasmic male sterility referred to is a stable and reliable sterility. More particularly preferably, this male sterility is not accompanied by female sterility. In fact, the seeds and plants that are preferred in the context of the present invention are female fertile.

Preferably, a seed of the genus *Diplotaxis* of the invention is a seed of the species *Diplotaxis tenuifolia*, and thus is diploid with 2n=22.

In a preferred embodiment, a seed of the invention comprises sequences deriving from *Raphanus sativus* in its mitochondrial DNA, as is the case for the plants of the invention, and more particularly sequences of the mitochondrial genome of *Raphanus sativus* CMS. In fact, the cytoplasmic male sterility is preferably derived from the cytoplasmic male sterility of *Raphanus sativus*, which results in the presence, in the mitochondrial genome of a seed of the invention, of sequences originating from *R. sativus* CMS.

Said sequences originating from the mitochondrial genome of *Raphanus sativus* preferably represent at least 50% of the mitochondrial genome of a seed of the invention, preferably at least 80%, or have a length of at least 50, or even at least 100, 200, 500 or 1000 consecutive base pairs.

In a preferred embodiment, the mitochondrial genome of a seed comprises the DNA sequence included between nucleotides 1673 and 2089 of FIG. 1 (SEQ ID No 1) or a sequence having at least 50% identity with said sequence and providing the cytoplasmic male sterility. Preferably, the mitochondrial genome of a seed in accordance with the invention comprises a sequence having at least 70%, at least 80%, or even at least 90% or 95% identity or at least 99% identity with said DNA sequence.

Particularly preferably, the portion of SEQ ID No 1 present in the genome of a seed in accordance with the invention provides the cytoplasmic male sterility.

Preferably, said portion corresponds to nucleotides 1673 to 2089 of SEQ ID No 1, which include the orf138. This sequence is characteristic of the cytoplasmic male sterility known as Ogura. Alternatively, said portion is a 512 base pair fragment corresponding to nucleotides 1579 to 2090 of SEQ ID No 1 comprising the orf138, or a 401 base pair fragment corresponding to nucleotides 1248 to 1648 of SEQ ID No 1, comprising all or a portion of the T-RNAt gene (Transfer-RNAt formylmethionine).

For this reason, a seed in accordance with the invention is preferably characterized by an amplified fragment of the following size, when the corresponding primers are used to amplify its mitochondrial genome by PCR:
  512 base pairs when the oligo primers 37 and 38 (SEQ ID No 22 and 23 respectively) are used; and/or
  401 base pairs when the primers TRNAFM-610U and TRNAFM-987L (SEQ ID No 24 and 25 respectively) are used.

Preferably, the sequence for the amplified fragment of 512 base pairs is SEQ ID No 20 and this sequence is present in the genome of a seed in accordance with the invention.

Preferably, the sequence for the amplified fragment of 401 base pairs is SEQ ID No 21 and this sequence is present in the genome of a seed in accordance with the invention.

The mitochondrial sequence initially described as being linked to the Ogura CMS in plants of the genus *Brassica* is the sequence mentioned in patent EP 0 549 726; variants of this sequence were then described, in particular those with accession numbers Z12626 and Z18896 (SEQ ID No 1).

Furthermore, in a preferred embodiment, a seed as described carrying cytoplasmic male sterility is also distinguished, in the chloroplastic genome, from another seed which does not carry said sterility via an intergeneric cross with a plant of the genus *Raphanus*.

Preferably, a seed of the invention comprises sequences which are not of the genus *Diplotaxis* in its chloroplasts, in the chloroplastic DNA. As an example, at least 50 base pairs of the chloroplastic genome are not from the genus *Diplotaxis*, preferably at least 100, or even at least 200 or 500, still more preferably at least a thousand bases. Preferably, the entire chloroplastic genome is not that of the genus *Diplotaxis*.

The portion of the chloroplastic genome which is not of the genus *Diplotaxis* is preferably of the genus *Raphanus*. Particularly preferably, it contains sequences deriving from the chloroplastic genome of *Raphanus sativus*. As described above, said sequences contain DNA sequences comprising at least 50 consecutive base pairs, preferably at least 100, at least 200 or even at least 500 base pairs. Preferably, the chloroplastic genome of a seed in accordance with the invention derives of the species *Raphanus sativus*, and so it contains no characteristic sequence of the chloroplastic genome of *B. rapa* or *B. oleracea*, or any other *Brassica*.

A seed in accordance with the invention is preferably characterized by an amplified fragment with the following size, when the corresponding primers are used to amplify its chloroplastic genome by PCR:
  193 base pairs when the oligo primers MF2_M13F and MF2_R (SEQ ID No 4 and 5 respectively) are used; and/or
  264 base pairs when the primers MF8_M13F and MF8_R (SEQ ID No 16 and 17 respectively) are used; and/or
  180 base pairs when the primers MF7_M13F and MF7_R (SEQ ID No 14 and 15 respectively) are used; and/or
  319 base pairs when the primers MF9_M13F and MF9_R (SEQ ID No 18 and 19 respectively) are used; and/or 303 base pairs when the primers MF3_M13F and MF3_R (SEQ ID No 6 and 7 respectively) are used; and/or 183 base pairs when the primers MF6_M13F and MF6_R (SEQ ID No 12 and 13 respectively) are used.

Example 2 illustrates this point.

The present invention also concerns plant cells of the genus *Diplotaxis*, which carry a cytoplasmic male sterility, preferably of the species *Diplotaxis tenuifolia*.

Preferably, a cell in accordance with the present invention derives from a plant or a seed as described above. It may be a cell at any stage of development or differentiation. It may be a reproductive cell, a callus, a root, leaf, apex, meristem cell or a cell from any other portion of the plant.

The cell in question may be isolated as a cluster or in a tissue. It may be in suspension or on a solid medium. Preferably, a cell in the context of the invention is a cell of the species *Diplotaxis tenuifolia* and is thus diploid, with 2n=22.

As explained above with regard to plants and seeds, a cell in accordance with one embodiment of the invention comprises sequences deriving from *Raphanus sativus* in its mitochondrial genome, preferably sequences originating from the mitochondrial genome of *Raphanus sativus* carrying cytoplasmic male sterility known as Ogura. Said sequences originating from the mitochondrial genome of *Raphanus sativus* preferably represent at least 50% of the mitochondrial genome of a cell of the invention, preferably at least 80%, or have a length of at least 50, or even at least 100, 200, 500 or 1000 consecutive base pairs.

In a preferred implementation, the mitochondrial genome of a cell comprises the DNA sequence included between nucleotides 1673 and 2089 of FIG. 1 (SEQ ID No 1) corresponding to the orf138 gene or a sequence having at least 50% identity with said sequence and providing the cytoplasmic male sterility. Preferably, the mitochondrial genome of a cell in accordance with the invention comprises a sequence having at least 70%, 80%, or even at least 90% or 95% identity or at least 99% identity with said DNA sequence, i.e. it has the cytoplasmic male sterility known as Ogura male sterility as described in the patent EP 0 549 726 from INRA.

Particularly preferably, the portion of SEQ ID No 1 present in the genome of a plant of the invention provides the cytoplasmic male sterility. Preferably, said portion corresponds to nucleotides 1673 to 2089 of SEQ ID No 1, which includes the orf138 gene.

This sequence is characteristic of the cytoplasmic male sterility known as Ogura sterility. Alternatively, said portion is a 512 base pair fragment corresponding to nucleotides 1579 to 2090 of SEQ ID No 1 comprising the orf138 gene, or a 401 base pair fragment corresponding to nucleotides 1248 to 1648 of SEQ ID No 1, comprising all or a portion of the T-RNAt gene (Transfer-RNAt formylmethionine).

For this reason, a cell in accordance with the invention is preferably characterized by an amplified fragment with the following size, when the corresponding primers are used to amplify its mitochondrial genome by PCR:

512 base pairs when the oligo primers 37 and 38 (SEQ ID No 22 and 23 respectively) are used; and/or 401 base pairs when the primers TRNAFM-610U and TRNAFM-987L (SEQ ID No 24 and 25 respectively) are used.

Preferably, the sequence for the amplified fragment of 512 base pairs is SEQ ID No 20 and this sequence is present in the genome of a cell in accordance with the invention.

Preferably, the sequence for the amplified fragment of 401 base pairs is SEQ ID No 21 and this sequence is present in the genome of a cell in accordance with the invention.

Furthermore, in a preferred embodiment, a plant cell as described carrying cytoplasmic male sterility is also distinguished, in the chloroplastic genome, from another cell of the species *Diplotaxis tenuifolia*. In particular, a cell of the invention preferably comprises sequences which are not of the genus *Diplotaxis* in its chloroplastic DNA. As already explained in relation to the plants and seeds of the invention, there may, for example, be at least 50 base pairs of the chloroplastic genome which are not of the genus *Diplotaxis*, preferably at least 100, or even at least 200 or 500, more preferably at least a thousand bases. Preferably, the entire chloroplastic genome is not that of the genus *Diplotaxis*.

The portion of the chloroplastic genome which is not of the genus *Diplotaxis* is preferably of the genus *Raphanus*. Particularly preferably, it concerns sequences originating from the chloroplastic genome of *Raphanus sativus*. As described above, "said sequences" means DNA sequences comprising at least 50 consecutive base pairs, or even at least 100, 200 or 500.

Preferably, the chloroplastic genome of a cell in accordance with the invention derives of the species *Raphanus sativus*, and so it contains no characteristic sequence of the chloroplastic genome of *B. rapa* or *B. oleracea*, or any other *Brassica*.

A cell in accordance with the invention is preferably characterized by an amplified fragment with the following size, when the corresponding primers are used to amplify the chloroplastic genome by PCR:

193 base pairs when the oligo primers MF2_M13F and MF2_R (SEQ ID No 4 and 5 respectively) are used; and/or 264 base pairs when the primers MF8_M13F and MF8_R (SEQ ID No 16 and 17 respectively) are used; and/or 180 base pairs when the primers MF7_M13F and MF7_R (SEQ ID No 14 and 15 respectively) are used; and/or 319 base pairs when the primers MF9_M13F and MF9_R (SEQ ID No 18 and 19 respectively) are used; and/or 303 base pairs when the primers MF3_M13F and MF3_R (SEQ ID No 6 and 7 respectively) are used; and/or 183 base pairs when the primers MF6_M13F and MF6_R (SEQ ID No 12 and 13 respectively) are used.

The present invention also pertains to various methods for obtaining plants, cells or seeds as described in the preceding sections.

In particular, the invention pertains to a method for obtaining a plant or a seed, preferably of the species *Diplotaxis tenuifolia*, comprising:

a) intergeneric crossing of a *Raphanus sativus* plant carrying cytoplasmic male sterility, as the female parent, and of a male fertile *Diplotaxis tenuifolia* plant, as the male parent;

b) obtaining a plant derived from the preceding cross by embryo rescue;

c) crossing a plant derived from step b), as the female parent, with a male fertile *Diplotaxis tenuifolia* plant, as the male parent;

d) obtaining a plant derived from cross c), optionally by embryo rescue.

*Raphanus sativus* plants with cytoplasmic male sterility are commercially available (for example the Clementine variety). This is also the case for *Diplotaxis tenuifolia* plants (male fertile), allowing to carry out the first intergeneric cross.

The inventors have shown that such an intergeneric cross can produce viable, male sterile hybrids. In order to achieve this, it is necessary, however, after fertilization, to remove siliques then the ovules and to culture them in vitro, i.e. to carry out a embryo rescue step. Using this technique, it is then possible to obtain and develop a plant corresponding to an intergeneric cross of a *Raphanus sativus* plant with cytoplasmic male sterility as the female parent, and a male fertile *Diplotaxis tenuifolia* plant as the male parent.

However, it should be noted that obtaining a plant derived from this cross may necessitate carrying out a large number of crosses and ovule cultures. The inventors have, however, repeated this intergeneric cross several times and have demonstrated the feasibility, viability and fertility (female) of such a cross (see Example 1).

It should be noted in this regard that the two species do not have the same number of chromosomes (2n=22 for *Diplotaxis tenuifolia* and 2n=18 for *Raphanus sativus*).

The method then includes a novel backcross with a plant of the species *Diplotaxis tenuifolia* used as the male parent, and obtaining another plant derived from this cross. At this stage also, it may be necessary to carry out an embryo rescue if no ovule develops in vivo. These steps of backcrossing and obtaining a plant (steps c) and d) of the method) may be repeated several times. They are preferably carried out at least twice or even at least three times in order that the plant obtained can be phenotypically of the species *Diplotaxis tenuifolia* or that it is a seed also of the species *Diplotaxis tenuifolia*, and thus is diploid and its number of chromosomes is equivalent to that of *Diplotaxis tenuifolia*, i.e. 2n=22.

After carrying out steps c) and d) the first or second time, it is generally of no use to carry out embryo rescue to obtain a viable plant.

In accordance with a preferred implementation of the method, the plants are obtained without any step for fusion of protoplasts being carried out. Preferably, there is also no step for inducing doubling of the number of chromosomes. However, this does not exclude doubling of the number of chromosomes occurring naturally, but preferably it does not happen.

The plants obtained by this method or the seeds derived therefrom carry cytoplasmic male sterility.

The invention also concerns plants, seeds and cells which can be obtained by implementing the method as described, and any biological material derived therefrom.

A plant, seed or cell that can be obtained by carrying out the method described is in particular characterized by its mitochondrial genome, carrying cytoplasmic male sterility, which preferably includes the portion corresponding to nucleotides 1673 to 2089 of SEQ ID No 1 (ORF138).

A plant, seed or cell that can be obtained by carrying out the method described is in particular characterized by its mitochondrial genome, preferably by an amplified fragment with the following size, when the corresponding primers are used to amplify the mitochondrial genome by PCR:
  512 base pairs when the oligo primers 37 and 38 (SEQ ID No 22 and 23 respectively) are used; and/or
  401 base pairs when the primers TRNAFM-610U and TRNAFM-987L (SEQ ID No 24 and 25 respectively) are used.

Preferably, the 512 base pair amplified sequence is SEQ ID No 20 and this sequence is present in the genome of a plant, seed or cell that can be obtained by carrying out the method of the invention.

Similarly, and preferably, the 401 base pair amplified sequence is SEQ ID No 21 and this sequence is present in the genome of a plant, seed or cell that can be obtained by carrying out the method of the invention.

A plant, seed or cell that can be obtained by carrying out the method described is also characterized by its chloroplastic genome, preferably by an amplified fragment with the following size, when the corresponding primers are used to amplify the chloroplastic genome by PCR:
  193 base pairs when the oligo primers MF2_M13F and MF2_R (SEQ ID No 4 and 5 respectively) are used; and/or
  264 base pairs when the primers MF8_M13F and MF8_R (SEQ ID No 16 and 17 respectively) are used; and/or
  180 base pairs when the primers MF7_M13F and MF7_R (SEQ ID No 14 and 15 respectively) are used; and/or
  319 base pairs when the primers MF9_M13F and MF9_R (SEQ ID No 18 and 19 respectively) are used; and/or
  303 base pairs when the primers MF3_M13F and MF3_R (SEQ ID No 6 and 7 respectively) are used; and/or
  183 base pairs when the primers MF6_M13F and MF6_R (SEQ ID No 12 and 13 respectively) are used.

Preferably, the chloroplastic genome of a plant, seed or cell that can be obtained by implementing the method described originates of the species *Raphanus sativus*, and so it contains no characteristic sequences of the chloroplastic genome of *B. rapa* or *B. oleracea*, or any other *Brassica*.

The embryo rescue optionally employed in the method is a technique that is well known to the skilled person and practised regularly in the case of intergeneric crosses or, more routinely, interspecific crosses. More particularly, this technique has been described in the publication by Rahman (2004) and its implementation is detailed in the experimental section of the application (example 1).

The various media, conditions and culture times for implementing this technique are described in the literature and may be adapted or modified if necessary. Examples thereof are given in the experimental section.

The present invention also concerns the use of a plant as described in the context of the present application as a female partner in a cross with another, male fertile, plant of the genus *Diplotaxis*. As an example, a plant of the species *Diplotaxis tenuifolia* as described in the application may be crossed with a plant of the genus *Diplotaxis* which is not male sterile.

Thus, by using a *D. tenuifolia* plant carrying cytoplasmic male sterility it is possible, using selection programs for example, to obtain for each known sub-species or variety of *Diplotaxis tenuifolia*, an equivalent sub-species or variety which is male sterile. It is also possible to obtain plants of the genus *Diplotaxis* and also species other than *Diplotaxis tenuifolia*, by carrying out a first interspecific cross followed by various back crosses. The cytoplasmic male sterility of a plant of the invention can thus be used as a vector for cytoplasmic male sterility in another *Diplotaxis* plant or in a *Diplotaxis tenuifolia* plant of another sub-species or variety.

The invention also concerns the use of a plant of the species *Raphanus sativus* carrying cytoplasmic male sterility, preferably the male sterility known as Ogura, as a vector for cytoplasmic male sterility in a *Diplotaxis* plant, preferably in a *Diplotaxis tenuifolia* plant.

As demonstrated in the experimental section below, surprisingly, the inventors have discovered that it is possible to transfer the known cytoplasmic male sterility of *Raphanus sativus* into plants of the species *Diplotaxis tenuifolia* by means of a single intergeneric cross without having recourse to protoplast fusion.

They have also demonstrated that the plants obtained were not affected by chlorosis, in contrast to the teaching of EP 0 549 726 which echoes the widespread prejudicial view held in personnel working in the field of the invention.

Thus, for the first time the inventors have obtained a plant from the Brassicaceae family but from a genus other than *Brassica* which carries cytoplasmic male sterility derived from *Raphanus sativus* and for which the chloroplastic genome is partly that of *Raphanus sativus*, i.e. it comprises at least 50 consecutive base pairs of *Raphanus sativus*, preferably at least 100, 200 or 500, and without being affected by chlorosis, especially at temperatures of less than 10° C.

KEY TO FIGURES

FIG. 1: This Figure illustrates the sequence SEQ ID NO: 1 corresponding to accession number Z18896, which comprises the sequence for the orf138 gene of the mitochondrial genome of *Raphanus sativus* CMS. The sequences corresponding to the oligo primers 37 and 38 (SEQ ID No 22 and 23 respectively) are double underlined; the sequence corresponding to the primers TRNAFM-610U and TRNAFM-987L (SEQ ID No 24 and 25 respectively) are single underlined.

FIG. 2: This Figure illustrates the result of agarose gel electrophoretic migration of various DNA samples after PCR amplification with the oligo primers 37 and oligo 38 (orf138, upper gel), with the primers TRNAFM-610U and TRNAFM-987L (T-RNAt, central gel) and with the primers COX1-244U and COX1-805L (cox1, lower gel). The first three wells (M1, M2 and M6) correspond to DNA samples from three lines of *R. sativus* CMS, the 4$^{th}$, 6$^{th}$ and 8$^{th}$ wells (M7, M9 and M11 respectively) correspond to DNA samples from fertile *D. tenuifolia* lines; the 5$^{th}$, 7$^{th}$ and 9$^{th}$ wells (M8, M10 and M12 respectively) correspond to DNA samples from various male sterile *Diplotaxis tenuifolia* plants of the invention.

F=fertile; S=sterile.

EXPERIMENTAL SECTION

Example 1: Production of Male Sterile *Diplotaxis tenuifolia* Plants (Cytoplasmic)

Summary of Study

The inventors crossed plants of the species *Raphanus sativus* carrying cytoplasmic male sterility (known as Ogura sterility) with fertile plants of the species *Diplotaxis tenuifolia*. They carried out several backcrosses in order to obtain a *Diplotaxis tenuifolia* nucleus while preserving the cytoplasmic male sterility. At the end of these various backcrosses, the plants obtained could be used as female parents for the production of hybrids.

More precisely, the inventors carried out crosses between plants of the species *Raphanus sativus* as the female parent carrying Ogura cytoplasmic male sterility, which are commercially available, with plants of the species *Diplotaxis tenuifolia* (fertile) as the male parent. They then obtained nine F1 plants by embryo rescue, resulting from this intergeneric cross.

In a second step, the inventors carried out a first backcross (backcross 1 or BC1) between the F1 plants obtained (*Raphanus sativus* CMS×*Diplotaxis tenuifolia*) and plants of the species *Diplotaxis tenuifolia*, i.e. the following scheme:

(*Raphanus sativus* CMS×*Diplotaxis tenuifolia*)× *Diplotaxis tenuifolia*

(using the international conventional whereby the female parent is mentioned on the side to the left of the cross and the male parent on the side to the right).

The climactic conditions meant that plants could not be obtained by embryo rescue, but repeating the same crosses the following year resulted in six plants which were male sterile.

The inventors then carried out a second backcross (BC2) using the following scheme:

((*Raphanus sativus* CMS×*Diplotaxis tenuifolia*)× *Diplotaxis tenuifolia*)×*Diplotaxis tenuifolia*.

An embryo was obtained by embryo rescue and resulted in several BC2 plants, which were also male sterile.

The following steps consisted of a third backcross, again with a plant of the species *Diplotaxis tenuifolia*, followed by a fourth backcross (BC4).

At the end of the fourth backcross, the plants obtained had all of the phenotypical characteristics characterizing the species *Diplotaxis tenuifolia* and could be used in selection programs, without it being necessary to resort to embryo rescue, especially to obtain parental cell lines carrying cytoplasmic male sterility ready for the production of hybrids.

Furthermore, the inventors carried out several hundred *B. Oleracea* (Ogura cytoplasmic male sterility)×*Diplotaxis tenuifolia* and *Brassica rapa* (Ogura cytoplasmic male sterility)×*Diplotaxis tenuifolia* crosses, but none of them resulted in the production of embryos.

More Detailed Description of the Various Steps:
1. Protocol for Intergeneric or Interspecific Crosses:
Hybridization of Flowers:

No special conditions; the usual protocol described in the literature was employed.

The crosses were of the type *B. rapa*×*D. tenuifolia*, *B. oleracea*×*D. tenuifolia*, *R. sativus*×*D. tenuifolia*, (*R. sativus*×*D. tenuifolia*)×*D. tenuifolia*, etc. . . .

Removal of Ovaries or Siliques:

The siliques were removed before they went yellow on the plant for culture (between 4 days and one month after crossing). Of the removed siliques, only the siliques that were more than 20 mm long with a larger diameter and blisters were used.

Disinfection:

The siliques were placed in tea ball infusers. They were washed with alcohol for 5 minutes. They were then washed with Bayrochlor solution, 3 cp/L of sterile water with a few drops of Tween 20 (polyoxyethylene sorbitan monolaurate) for 30 minutes, agitating the tea ball infuser regularly. They were then rinsed three times more with sterile water, agitating the tea ball infuser occasionally.

Culture of Ovules:

Of the removed siliques, only those which had changed were open. They were the siliques that were more than 20 mm long with a larger diameter.

The siliques were opened along the dehiscence split using a lance-shaped needle. Well rounded and whitish ovules were removed. They were cultured so that the hilum was in contact with the gelose in order to allow the embryo to develop.

The cultured ovules were observed regularly and transplanted every two weeks. The ovules that turned black and/or went flat (which is synonymous with abortion) were eliminated.

Culture Conditions for the Culture of Ovaries and Ovules

N6 medium, in diffuse light with a photoperiod of 16 hours, at a temperature of 22° C. during the daylight periods and 20° C. during the nighttime period. The composition of this N6 medium is detailed in the publications by Chu, 1978 and Chu et al, 1975.

1. Development and Multiplication of Plantules Obtained from Embryos.

Composition of the Various Culture Media for the Development and Multiplication of the Plantules Obtained:

Mi01 medium is a base medium from Murashige and Skoog (Murashige and Skoog, 1962) supplemented with Morel vitamin B1, saccharose and Agar-Agar as the gelling agent. The pH of Mi01 medium is 5.8.

Mi55 medium is a base medium from Murashige and Skoog (Murashige and Skoog, 1962) supplemented with Morel vitamin B1, saccharose and Gelrite as the gelling agent, with $Ga_3$ growth compound after autoclaving. The pH of Mi55 medium is 5.9/6.

Development of Embryos:

The embryos appeared between 1 and 1½ months after placing the ovules in culture. The embryos were placed in direct light with a photoperiod of 16 hours, a temperature of 22° C. during the daylight periods and 20° C. during the night time periods.

The embryos can change in two manners: either they form a plantule or a callus forms, regenerating various plantules. The cultured embryos did not immediately produce plantules; there was callus formation, occasionally with buds on top.

The plantules were isolated on a development medium, medium 01 (or Mi01).

Multiplication of Explants

For the Calluses:

The calluses were transplanted onto an induction medium, N6 or Mi55, to regenerate the buds. The buds were transplanted onto Mi01 medium.

For the Buds:

All of the buds from the calluses were subcultured on Mi01 development medium to make them root.

Summary:

for the development and the multiplication of explants, two cases are possible:

1) Via the callus. Callus culture was carried out on an induction medium. The calluses regenerated buds;
2) buds were available which could be developed directly. This culture was carried out on Mi01 development medium.

In order to multiply these plantules, if the plantule had no problems with development, the culture of nodes was used, on Mi01 medium. These nodes (or axillary buds) developed into plantules.

If the plantule was stunted and/or there were developmental problems, it was transplanted onto Mi55 multiplication medium.

Rooting the Plantules:

To root the multiplied plantules, for acclimation, they were cultivated on Mi01 rooting medium.

Acclimation:

The inventors then carried out acclimation as soon as the plantules had well developed roots. In vitro culture was continued until such roots had been obtained.

The plants were acclimated in individual pots with a Klasmann Potgrong H horticultural substrate and kept in a mini greenhouse for one week. After one week, the inventors obtained good plants with good roots which were removed from the mini greenhouses.

After three weeks, the plants had a good root system and good leaf development. The plants were then planted in open ground in a tunnel.

Phenotyping of the plants obtained was carried out in order to select those for which the phenotypical characteristics were closest to *Diplotaxis tenuifolia* while carrying cytoplasmic male sterility (detectable phenotypically due to the absence of pollen).

3. Results

Intergeneric Crosses

The inventors carried out the following intergeneric crosses:

*Brassica rapa* CMS×*Diplotaxis tenuifolia* and *B. oleracea* CMS×*Diplotaxis tenuifolia*, followed by the following backcrosses:

(*Brassica rapa* CMS×*Diplotaxis tenuifolia*)×*Diplotaxis tenuifolia* and (*B. oleracea* CMS×*Diplotaxis tenuifolia*)×*Diplotaxis tenuifolia*.

No embryos were obtained for these two backcrosses, and thus no descendants.

The inventors then carried out the following intergeneric cross:

*Raphanus sativus* (CMS)×*Diplotaxis tenuifolia*.

The siliques were removed and the ovaries were cultured. In total, 135 *Raphanus sativus* (CMS)×*Diplotaxis tenuifolia* hybridizations were carried out, 1857 siliques were removed and 207 ovules were cultured; using this technique, 9 embryos were obtained, and given the codes RD1 to RD9.

Plants were thus obtained in vitro; they were then acclimated.

First Backcross:

The following year, the inventors carried out a first backcross using the scheme:

[*Raphanus sativus* (CMS)×*Diplotaxis tenuifolia*]× *Diplotaxis tenuifolia*.

Table 1 summarizes the number of siliques removed with ovules.

TABLE 1

| Code of female parent | No of siliques removed | No of siliques with ovules | % of siliques with ovules | No of ovules cultured |
|---|---|---|---|---|
| RD1 | 49 | 22 | 44.9% | 400 |
| RD1 | 100 | 42 | 42% | 635 |
| RD2 | 0 | 0 | | 0 |
| RD2 | 0 | 0 | | 0 |
| RD4 | 12 | 8 | 66.7% | 161 |
| RD4 | 55 | 32 | 58.2% | 561 |
| RD5 | 38 | 2 | 5.3% | 2 |
| RD8 | 10 | 3 | 30% | 4 |
| RD8 | 26 | 1 | 3.8% | 2 |
| RD8 | 10 | 2 | 20% | 2 |
| RD8 | 15 | 6 | 40% | 13 |
| RD9 | 38 | 14 | 36.8% | 224 |
| RD9 | 72 | 34 | 47.2% | 887 |
| Total | 425 | 166 | 39.1% | 2891 |

The number of siliques containing ovules was mediocre (mean frequency 39.1%).

The ovules were transplanted twice onto fresh N6 medium. No BC1 embryos were obtained for the 2891 ovules that were cultured. However, it should be noted that the first crosses were carried out under poor climactic conditions.

The inventors then carried out a fresh backcross trial the following year, modifying the fertilization method compared with the preceding year. It was decided not to carry out all of the fertilizations simultaneously, but to spread them over a month in order to limit the influence of climatic conditions, and to produce at most 200 buds each day of fertilization.

Table 2 summarizes the results of this second backcross trial.

| Code of female parent | No of siliques removed | No of ovules cultured | No of germinated ovules | No of embryos obtained | Code of plants obtained |
|---|---|---|---|---|---|
| RD8 | 24 | 58 | 0 | | |
| RD8 | 6 | 0 | 0 | | |
| RD9 | 50 | 205 | 1 | 0 | 0 |
| RD3 | 6 | 0 | 0 | | |
| RD3 | 0 | 0 | 0 | | |
| RD6 | 0 | 0 | 0 | | |
| RD6 | 3 | 4 | 0 | | |
| RD8 | 36 | 0 | 0 | | |
| RD8 | 24 | 2 | 1 | | |
| RD2 | 40 | 0 | 0 | | |
| RD8 | 33 | 10 | 0 | | |
| RD9 | 21 | 80 | 0 | | |
| RD3 | 0 | 0 | 0 | | |
| RD8 | 25 | 11 | 4 | 2 | D6-D7 |
| RD9 | 38 | 168 | 0 | | |
| RD2 | 0 | 0 | 0 | | |
| RD3 | 0 | 0 | 0 | | |
| RD8 | 31 | 80 | 0 | | |
| RD8 | 32 | 7 | 0 | | |
| RD8 | 21 | 73 | 0 | | |
| RD9 | 15 | 140 | 0 | | |
| RD9 | 24 | 61 | 0 | | |
| RD8 | 23 | 50 | 0 | | |
| RD8 | 0 | 0 | 0 | | |
| RD8 | 56 | 130 | 0 | | |
| RD8 | 32 | 119 | 0 | | |
| RD9 | 27 | 100 | 1 | 1 | D4 |
| RD8 | 58 | 111 | 0 | | |
| RD8 | 27 | 141 | 0 | | |
| RD8 | 14 | 19 | 0 | | |
| RD8 | 21 | 380 | 3 | 4 | D1-D2-D3-D5 |
| RD3 | 7 | 0 | 0 | | |
| RD8 | 26 | 8 | 0 | | |
| Total | 720 | 1957 | 10 | 7 | |

As can be seen from this Table 2, 7 embryos were obtained in total, denoted D1 to D7. Plantule D7 did not develop.

Transplanting the embryos onto N6 medium allowed buds to proliferate: each embryo could then be cloned into several copies. It was then possible to acclimate the plants which would then be used in the following backcrosses, all the while keeping the plantules in vitro.

The F1 and BC1 material was also kept permanently in vitro or in a greenhouse (when contamination problems arose).

The acclimated plants were cultured from axillaries. The stem sections were disinfected with a solution of Bayrochlor solution (3 cp/L) for 30 minutes. The axillaries were deposited on a base medium (for example Mi01).

Second Backcross:

The inventors then carried out the second backcross using the scheme:

[[*Raphanus sativus* (CMS)×*Diplotaxis tenuifolia*]× *Diplotaxis tenuifolia*]×*Diplotaxis tenuifolia*

The siliques were removed a few days after hybridization, in order to culture the ovules.

With the 60 hybridizations carried out, 1149 siliques were removed and 5505 ovules were cultured.

A single embryo was obtained; it was transplanted every two weeks onto Mi55 or N6 medium to obtain a callus then buds which developed into plantules.

Example 2: Characterization of Mitochondrial and Chloroplastic Genome of *Diplotaxis tenuifolia* Plants In Brassicaceae, the chloroplastic genome and the mitochondrial genome are characterized by exclusively maternal heredity. The inventors used three mitochondrial genes described in patent EP 0 549 726 and chloroplastic microsatellite markers (or SSR for "simple sequence repeat") described in the publication by Flannery et al (2006), in order to characterize the male cytoplasm in the male sterile *Diplotaxis tenuifolia* plants of the invention.

It should be recalled that the mitochondrial genome and chloroplastic genome of a *Diplotaxis tenuifolia* plant of the invention comprises sequences originating from *Raphanus sativus*.

The oligonucleotides defined within the orf138 gene and the formylmethionine transfer RNAt gene respectively allow amplification of a 512 and 401 base pair fragment, only in plants comprising Ogura sterility.

Amplification in the cox I gene (small sub-unit 1 of cytochrome oxidase) of a 655 base pair fragment of the mitochondrial genome of radish acted as a control in that said fragment had to be amplified in all of the lines tested.

The presence or absence of amplification of fragments of mitochondrial sequences using said primers could be used to characterize the various plants employed in the present invention as regards their cytoplasmic male sterility.

The allelic variation of the SSR chloroplastic microsatellite markers tested allowed the provenance of the chloroplastic genome of the *Diplotaxis tenuifolia* plants of the invention to be characterized, and more particularly the presence of chloroplastic sequences characteristic of *Raphanus sativus*.

The length of the fragment of the chloroplastic sequences amplified using these primers could be employed to characterize the various plants used in the present invention as regards the nature of their chloroplastic genome.

The chloroplastic genome of the *Diplotaxis tenuifolia* plants obtained using the method described in this invention differ from other *Diplotaxis tenuifolia* plants for which their chloroplastic genome does not originate from the genus *Raphanus*.

A. Analysis of Mitochondrial Markers and PCR Conditions

Total DNA (nuclear and cytoplasmic genomes) of fertile and male sterile *Diplotaxis tenuifolia* plants of the invention was isolated from the leaves of 8 week old plants using the protocol developed by Dellaporta (1983).

Use of specific markers of the orf138 and T-RNAt genes in order to detect Ogura cytoplasmic male sterility:

```
Orf138
"Sense" primer: oligo 37:
                                      (SEQ ID No 22)
5'-GCATCACTCTCCCTGTCGTTATCG-3'  (8 µM);

"Antisense" primer: oligo38:
                                      (SEQ ID No 23)
5'-ATTATTTTCTCGGTCCATTTTCCA-3'  (8 µM).
```

-continued

```
T-RNAt
"Sense" primer: TRNAFM-610U:
                                    (SEQ ID No 24)
5'-ACGTGTAGCCCTGTATGGACT-3' (8 µM);

"Antisense" primer: TRNAFM-987L:
                                    (SEQ ID No 25)
5'-GGTATTGTCACTTCCCGTTTC-3' (8 µM).
```

The position of these various primers is illustrated in FIG. 1 (underlined for the primers linked to T-RNAt and double underlined for the primers linked to orf138).

Use of specific markers to amplify a positive mitochondrial control in all of the tested plants:

```
"Sense" primer: COX1-244U:
                                    (SEQ ID No 26)
5'-GGTAATTGGTTTGTTCCGATT-3' (8 µM);

"Antisense" primer: COX1-805L:
                                    (SEQ ID No 27)
5'-CATGCCTAGATACCCGAAGAC-3' (8 µM).
```

The PCR reaction for these markers was carried out on 20 µl samples comprising:
5.0 µL of diluted total DNA (2 to 10 ng/µL)
2.0 µL of 10×PCR buffer (Invitrogen)
2.0 µL of MgCl$_2$ 25 mM (Invitrogen)
1.5 µL of dNTP mixture (2 mM of each dNTP; SIGMA)
0.7 µL "sense primer" (8 µM)
0.7 µL "antisense primer" (8 µM)
0.15 µL ADN Taq polymerase, 5 U/µL (Invitrogen)
7.95 µL H$_2$O.

The profile of the PCR thermocycles was as follows:
for the amplification of ORF138 and T-RNAt:
3 minutes at 94° C.; then 35 cycles of (30 sec at 94° C., 45 sec at 68.5° C., 1 min at 72° C.); 7 min at 72° C. then back down to 4° C., on a PCT GeneAmp® 2700 system (Applied Biosystems).
for the amplification of COX1:
3 minutes at 94° C.; then 35 cycles of (30 sec at 94° C., 45 sec at 54° C., 1 min at 72° C.); 7 min at 72° C. then back down to 4° C., on a PCT GeneAmp® 2700 system (Applied Biosystems).

A portion of the PCR products was checked on 1.5% agarose gel and the remainder underwent sequencing using Sanger's method.

FIG. 2 shows a band corresponding to amplification of COX1 for all of the samples. The amplification bands representing the fragments of ORF138 and T-RNAt were only present in columns loaded with mitochondrial DNA from plants carrying Ogura cytoplasmic male sterility.

The scale shown on the left hand side of the gel confirms that the amplified fragments were of a size in agreement with prediction, i.e. approximately 512 base pairs for ORF138, approximately 401 for T-RNAt and approximately 655 for COX1.

The inventors also sequenced two amplified fragments (ORF138 and T-RNAt), which confirmed that their size was in agreement with the expected sizes, but also that the sequence of the amplified fragments was identical or almost identical to the sequence listed as being linked to the Ogura CMS in *Raphanus sativus*, namely Z18896.

Sequencing of the amplified fragments (consensus of sequencing of several fragments) produced the following results (the underlined sequences correspond to the sequences for the primers):

512 base pair fragment of orf138:

```
                                                (SEQ ID No 20)
GCATCACTCTCCCTGTCGTTATCGACCTCGCAAGGTTTTTGAGACGGCCG

AAACGGGAAGTGACAATACCGCTTTTCTTCAGCATATAAATGCAATGATT

ACCTTTTTCGAAAAATTGTCCACTTTTTGTCATAATCTCACTCCTACTGA

ATGTAAAGTTAGTGTAATAAGTTTCTTTCTTTTAGCTTTTTTACTAATGG

CCCATATTTGGCTAAGCTGGTTTTCTAACAACCAACATTGTTTACGAACC

ATGAGACATCTAGAGAAGTTAAAAATTCCATATGAATTTCAGTATGGGTG

GCTAGGTGTCAAAATTACAATAAAATCAAATGTACCTAACGATGAAGTGA

CGAAAAAAGTCTCACCTATCATTAAAGGGGAAATAGAGGGGAAAGAGGAA

AAAAAAGAGGGGAAAGGGGAAATAGAGGGGAAAGAGGAAAAAAAAGAGGG

GAAAGGGGAAATAGAGGGGAAAGAGGAAAAAAAAGAGGTGGAAAATGGAC

CGAGAAAATAAT.
```

A single difference in one nucleotide (position 43 of SEQ ID No 20) was revealed compared with the corresponding sequence of Z18896 (SEQ ID No 1).

401 base pair fragment of T-RNAt:

```
                                                (SEQ ID No 21)
ACGTGTAGCCCTGTATGGACTCGCGAAGCAGGTCTCCGGTCGGTGTCCAA

GATTTGATCTAACTATTGAGTGAGGACTACTTACCGATTGATAGAATAAT

ACGTATATAAGAAGAAGGCTGCTTTGTGGAGTGATCTTTCTCGAAATGAA

TTAAGTAAGGGCGCTATGTTCAGATTCTGAACCAAAGCACTAGTTGAGGT

CTGAAAGCCTTATGAGCAGAAGTAATAAATACCTCGGGGAAGAAGCGGGG

TAGAGGAATTGGTCAACTCATCAGGCTCATGACCTGAAGATTACAGGTTC

AAATCCTGTCCCCGCACCGTAGTTTCATTCTGCATCACTCTCCCTGTCGT

TATCGACCTCGCAAGGTTTTTGAAACGGCCGAAACGGGAAGTGACAATAC

C.
```

No divergences were observed between SEQ ID NO: 21 and the corresponding sequence of Z18896 (SEQ ID No 1).

This means that it can be concluded that the mitochondrial genome of male sterile *Diplotaxis tenuifolia* plants in accordance with the present invention is indeed that of the female parent in the intergeneric cross, i.e. that of *Raphanus sativus* CMS.

B. Analysis of Chloroplastic Markers and PCR Conditions

Use of SSR (simple sequence repeat or microsatellite marker) to distinguish between fertile plants and plants carrying the cytoplasmic male sterility of the invention.

The markers used are shown in Table 3.

Polymorphism analysis of the SSR markers was carried out on a MegaBACE® DNA analysis system with the aid of a LPA high resolution separation matrix with a resolution to a single base (General Electrics Healthcare Inc).

These SSR markers were amplified using the M13 tail universal primer to amplify many SSR fragments targeted using a single labeled M13 primer (various dyes available, such as FAM, HEX or NED) and many "sense" M13 primers.

The reaction medium for the PCR consisted of a 100 µL sample comprising:

5.0 µL of diluted total DNA (2 to 10 ng/µL)
1.0 µL of 10×PCR buffer (Invitrogen)
1.0 µL of MgCl₂ 25 mM (Invitrogen)
1.0 µL of dNTP mixture (2 mM of each dNTP; SIGMA)
0.6 µL "sense primer"-M13 (2 µM)
0.6 µL "antisense primer" (8 µM)
0.12 µL M13 primer labeled with FAM, HEX or NED (8 µM)
0.12 µL DNA Taq polymerase 5 U/µL (Invitrogen)
0.56 µL H₂O.

The profile for the PCR thermocycles was as follows:

3 minutes at 94° C.; then 35 cycles of (15 sec at 94° C., 20 sec at 50° C., 15 sec at 72° C.); 7 min at 72° C. then back down to 4° C., on a GeneAmp® 2700 PCT system (Applied Biosystems).

The genotyping analysis was carried out on a MegaBACE®.

Four to six SSR products were diluted to one twentieth and multiplexed in the same capillary with 5 µL of ET-400 ROX (standard size scale). The conditions of use were as follows:
Injection time: 110 seconds;
Voltage on injection: 3 kV;
Run time: 65 minutes
Voltage during run: 9 kV
Filters: dye set II The MegaBACE® Fragment Profiler 1.0 program can convert raw data into size-related data. Table 4 contains the SSR alleles obtained for the various fertile and male sterile plants of the present invention.

The analysis was carried out on 2 different lines of fertile *Diplotaxis tenuifolia* and on 2 lines of *Diplotaxis tenuifolia* of the present invention, as well as on one line of *Brassica oleracea* carrying Ogura cytoplasmic male sterility in accordance with patent EP 0 549 726 and on the *Raphanus sativus* line carrying Ogura cytoplasmic male sterility.

TABLE 3

Primers used for chloroplastic genotyping.

| Primer | Sequence | SEQ ID | Gene |
|---|---|---|---|
| MF1_M13F | 5'-CACGACGTTGTAAAACGACTCAATTGCACATTCTAGAATTCTAAG-3' | SEQ ID No 2 | trnL-F gene |
| MF1_R | 5'-CAATTCAATATGGTTATATATTAGAG-3' | SEQ ID No 3 | |
| MF2_M13F | 5'-CACGACGTTGTAAAACGACGGTTCCGTCGTTCCCATCGC-3' | SEQ ID No 4 | RPL16 gene |
| MF2_R | 5'-CATAATAATTAGATAAATCTGTTCC-3' | SEQ ID No 5 | |
| MF3_M13F | 5'-CACGACGTTGTAAAACGACAATGGTATGACTAGCTTATAAGG-3' | SEQ ID No 6 | trnE-trnT gene |
| MF3_R | 5'-CTTAACAATGAGATGAGGCAATC-3' | SEQ ID No 7 | |
| MF4_M13F | 5'-CACGACGTTGTAAAACGACCGGATCTATTATGACATATCC-3' | SEQ ID No 8 | psaA-ycf3 gene |
| MF4_R | 5'-GAAATATGAATACACTAGATTAGG-3' | SEQ ID No 9 | |
| MF5_M13F | 5'-CACGACGTTGTAAAACGACCCTGGCGGTATCAAGATGCCACT-3' | SEQ ID No 10 | trnT-rpoC2 gene |
| MF5_R | 5'-GCCATAATGGTACAGAACTAT-3' | SEQ ID No 11 | |
| MF6_M13F | 5'-CACGACGTTGTAAAACGACGAAGGAATAGTCGTTTTCAAG-3' | SEQ ID No 12 | atpB-rbcL gene |
| MF6_R | 5'-CATAATTAGAGTTCCATTTCGG-3' | SEQ ID No 13 | |
| MF7_M13F | 5'-CACGACGTTGTAAAACGACCGGCAGGAGTCATTGGTTCAAA-3' | SEQ ID No 14 | TrnM-atpE gene |
| MF7_R | 5'-GATTTTGTAACTAGCTGACG-3' | SEQ ID No 15 | |
| MF8_M13F | 5'-CACGACGTTGTAAAACGACCTTATATTCATAAGCGAAGAAC-3' | SEQ ID No 16 | rbcL-accD gene |
| MF8_R | 5'-AATAACAATAGATGAATAGTCA-3' | SEQ ID No 17 | |
| MF9_M13F | 5'-CACGACGTTGTAAAACGACGGGCCGTTATGCTCATTACG-3' | SEQ ID No 18 | ndhB-rps7 gene |
| MF9_R | 5'-TCCTATTCATGGGGATTCCG-3' | SEQ ID No 19 | |

TABLE 4

Results of genotyping with 9 chloroplastic SSRs. The numbers represent the size of the alleles of the amplification fragments as the number of bases

|  | MF1 | MF2 | MF8 | MF7 | MF9 | MF4 | MF3 | MF5 | MF6 |
|---|---|---|---|---|---|---|---|---|---|
| B. oleracea CMS (patent EP 0 549 726) | 184 | 190 | 265 | 170 | 328 | 160 | 306 | 218 | 178 |
| Raphanus sativus CMS Ogura | 183 | 193 | 264 | 180 | 319 | 158 | 303 | 218 | 183 |
| D. tenuifolia 1 | 183 | 190 | 146 | 173 | 327 | 164 | 298 | 218 | 176 |
| D. tenuifolia 3 | 183 | 191 | 147 | 173 | 327 | 158 | 312 | 218 | 180 |
| CMS D. tenuifolia 1 | 183 | 193 | 264 | 180 | 319 | 158 | 303 | 218 | 183 |
| CMS D. tenuifolia 2 | 183 | 193 | 264 | 180 | 319 | 158 | 303 | 218 | 183 |

It will be recalled that the chloroplasts of a *Diplotaxis tenuifolia* plant of the invention originate from *Raphanus sativus*.

In plants of the *Brassica oleracea* type carrying Ogura cytoplasmic male sterility, following the fusion of protoplasts to allow the cytoplasmic male sterility of *Raphanus sativus* to be imported into *Brassica oleracea*, the chloroplasts are distinguished from those of *Raphanus sativus*.

The results of Table 4 confirm that the lengths of the amplified fragments are identical for the 2 *Diplotaxis tenuifolia* lines of the present invention (i.e. CMS, the last two lines of the table), and these lengths are also identical to those of the amplified fragments for the Ogura male sterile *Raphanus sativus* line. This means that it can be concluded that the chloroplastic genome of male sterile *Diplotaxis tenuifolia* plants of the present invention does indeed originate from *Raphanus sativus* (used as the female parent in the intergeneric cross).

The results obtained relating to the chloroplastic genome confirm that the chloroplastic genome of the plants of the invention correspond to the chloroplastic genome of *Raphanus sativus* and that it is distinguished from the chloroplastic genome of plants such as those described in patent EP 0 549 726.

Furthermore, the chloroplastic genome of the plants of the invention, carrying cytoplasmic male sterility, are also distinguished from that of male fertile plants of the species *Diplotaxis tenuifolia*.

In order to distinguish between a male sterile *Diplotaxis tenuifolia* plant of the present invention and a fertile *Diplotaxis tenuifolia* plant, the following pairs of markers are particularly suitable:

the oligo primers MF2_M13F and MF2_R (SEQ ID No 4 and 5 respectively), which can produce a 193 base pair amplification fragment, characteristic of the chloroplastic genome of *Raphanus sativus*;

the oligo primers MF8_M13F and MF8_R (SEQ ID No 16 and 17 respectively), which can produce a 264 base pair amplification fragment, characteristic of the chloroplastic genome of *Raphanus sativus*;

the oligo primers MF8_MF7_M13F and MF7_R (SEQ ID No 14 and 15 respectively), which can produce a 180 base pair amplification fragment, characteristic of the chloroplastic genome of *Raphanus sativus*;

the oligo primers MF9_M13F and MF9_R (SEQ TD No 18 and 19 respectively), which can produce a 319 base pair amplification fragment, characteristic of the chloroplastic genome of *Raphanus sativus*;

the oligo primers MF3_M13F and MF3_R (SEQ ID No 6 and 7 respectively), which can produce a 303 base pair amplification fragment, characteristic of the chloroplastic genome of *Raphanus sativus*;

the oligo primers MF6_M13F and MF6_R (SEQ ID No 12 and 13 respectively), which can produce a 183 base pair amplification fragment, characteristic of the chloroplastic genome of *Raphanus sativus*;

the oligo primers 37 and 38 (SEQ ID No 22 and 23 respectively), which can produce a 512 base pair amplification fragment, characteristic of the mitochondrial genome of *Raphanus sativus* CMS (Ogura);

the primers TRNAFM-610U and TRNAFM-987L (SEQ ID No 24 and 25 respectively), which can produce a 401 base pair amplification fragment, characteristic of the mitochondrial genome of *Raphanus sativus* CMS (Ogura).

BIBLIOGRAPHY

Cao J. and Earle, E. D. Plant Cell Report 21:789-796 (2003).

Chu C. C *The N-medium and its application to anther culture of Cereal crops* Proc. Symp. Plant Tissue culture, Peking 43 (1978).

Chu C. C et al *Establishment of an efficient medium for anther culture of Rice through comparative experiments on the nitrogen sources*, Scienta Sinic, 18, 659 (1975).

Flannery M. L. et al. *Plastid genome characterization in Brassica and Brassicaceae using a new set of nine SSRs.* Theor Appl Genet 113:1221-1231 (2006).

Matsuzawa et al. *Male sterility in alloplasmic Brassica rapa L. carrying Eruca sativa cytoplasm.* Plant Breeding 118, 82-84 (1999).

Murashige, T. and Skoog F. *A revised medium for rapid growth and bioassays with tobacco tissue cultures.* Physiol. Plant 15, 473 (1962)

Rahman, M. H. *Optimum age of siliques for rescue of hybrid embryos from crosses between Brassica oleracea, B. rapa and B. carinata.* Canadian Journal of Plant Science 84 (4): 965-969 (2004).

Woo Bang, S. et al. (2003). Production of Intergeneric Hybrids between the C3-C4 Intermediate Species *Diplotaxis tenuifolia* (L.) DC. and *Raphanus sativus* L. Breeding Sciences 53: 231-236

The invention claimed is:

1. A seed of the species *Diplotaxis tenuifolia*, wherein said seed produces a plant having cytoplasmic male sterility and wherein cells of said plant comprise, in their chloroplastic genome, the chloroplastic DNA of *Raphanus sativus* CMS Ogura.

2. The seed according to claim 1, wherein its cells comprise, in their mitochondrial genome, a portion of the DNA sequence SEQ ID No 1 or a sequence having at least 70% identity with said DNA sequence.

3. The seed according to claim 1, wherein the presence of the chloroplastic genome of *Raphanus sativus* CMS Ogura in a plant grown from said seed can be tested by comparing the size of the amplification fragment obtained when the primer pair SEQ ID Nos 4 and 5 is used to amplify by PCR the chloroplastic genome of said plant with the size of the amplification fragment obtained for a *R. sativus* CMS Ogura plant.

4. The seed according to claim 1, wherein cells in a plant grown from said seed have the genomic DNA of *Diplotaxis tenuifolia* and the mitochondrial and chloroplastic DNA of *Raphanus sativus* CMS Ogura.

5. A plant of the species *Diplotaxis tenuifolia*, having cytoplasmic male sterility, grown from a seed according to claim 1.

6. The plant according to claim 5, having no symptoms of chlorosis under normal culture conditions.

7. The plant of claim 6, having no discoloration of leaves due to a lack of chlorophyll.

8. The plant according to claim 5, wherein said plant is a hybrid plant.

9. A cell of a plant of the species *Diplotaxis tenuifolia*, having cytoplasmic male sterility, wherein said cell comprises, in its chloroplastic genome, the chloroplastic DNA of *Raphanus sativus* CMS Ogura.

10. A cell of a plant of the species *Diplotaxis tenuifolia* Diplotaxis, having cytoplasmic male sterility, wherein said cell comprises, in its chloroplastic genome, the chloroplastic DNA of *Raphanus sativus* CMS Ogura, wherein said cell originates from a plant according to claim 5.

11. A cell of a plant of the species *Diplotaxis tenuifolia*, having cytoplasmic male sterility, wherein said cell comprises, in its chloroplastic genome, the chloroplastic DNA of *Raphanus sativus* CMS Ogura, wherein said cell originates from a seed according to claim 1.

12. A method for transferring a cytoplasmic male sterility in a male fertile plant of the genus *Diplotaxis*, comprising:
crossing a plant according to claim 1, as a female parent, with said male fertile plant,
thus transferring the cytoplasmic male sterility to the male fertile plant of the genus *Diplotaxis*.

13. The seed according to claim 1, wherein the presence of the chlorolastic genome of *Raphanus sativus* CMS Ogura in a plant grown from said seed can be tested by comparing the size of the amplification fragment obtained when the primer pair SEQ ID Nos 14 and 15 is used to amplify by PCR the chloroplastic genome of said plant with the size of the amplification fragment obtained for a *R. sativus* CMS Ogura plant.

14. The seed according to claim 1, wherein the presence of the chlorolastic genome of *Raphanus sativus* CMS Ogura in a plant grown from said seed can be tested by comparing the size of the amplification fragment obtained when the primer pair SEQ ID Nos 18 and 19 is used to amplify by PCR the chloroplastic genome of said plant with the size of the amplification fragment obtained for a *R. sativus* CMS Ogura plant.

15. The seed according to claim 1, wherein the presence of the chlorolastic genome of *Raphanus sativus* CMS Ogura in a plant grown from said seed can be tested by comparing the size of the amplification fragment obtained when the primer pair SEQ ID Nos 6 and 7 is used to amplify by PCR the chloroplastic genome of said plant with the size of the amplification fragment obtained for a *R. sativus* CMS Ogura plant.

16. The seed according to claim 1, wherein the presence of the chlorolastic genome of *Raphanus sativus* CMS Ogura in a plant grown from said seed can be tested by comparing the size of the amplification fragment obtained when the primer pair SEQ ID Nos 12 and 13 is used to amplify by PCR the chloroplastic genome of said plant with the size of the amplification fragment obtained for a *R. sativus* CMS Ogura plant.

* * * * *

SEQUENCE LISTING

<160> NUMBER OF SEQ ID NOS: 27

<210> SEQ ID NO 1
<211> LENGTH: 3293
<212> TYPE: DNA

<213> ORGANISM: Raphanus sativus

<400> SEQUENCE: 1

```
aagcttgaag ggtaatatct tcgccaccct cccgactcgc aatccccaat gtggctttcc      60
tcacttcggt aagttacaag gatgaatgca aatagcaagg cgctatgctg cgtgaagtga     120
gaccggctgt cctaagttaa gttgcttcct tattcattaa tgatcttgct cagtaggagg     180
gcttttcccc ttctgtgcag cctgatttta tctctggaaa tgagggtgcc ctcgattgca     240
attttcatc gaatatgatg gattccccccc atggtgagaa ggttgagtta cagactccgt     300
tggctttcgc aagacagtct cgaaagttcc gaaatctatg gttgatgtct cactcgaact     360
ctatccctga ctttcttcgt ccgagcggcc cctctaggag ccgatgcggg aaggaagaag     420
gatttatttc taccattaaa taattcgcaa tagttaacca agcagtagcc aagaacaaag     480
aagcaagcca agatcaatgg gggggtcgc cccagtcaaa aatggtaaga aggagtagca     540
tcaataacat tcattgtatg tacgcctccc agcgatccac aggcatctgt agcatgttgt     600
acccgagagt tattttggct gtgtctgtta caccatggac aataatctta gtcggagtca     660
aattccttac ctttccaccc aaagctgaac atatccgcac agatattcca tttttttat      720
tgaggatcca ttttcgaact gaactactca tgcttaggca aaacaagcaa gggagttgtt     780
aataaggagc tagctacagt gctcctgcgg gagggttccc gtgcttatta aggagccggg     840
cagctacgca acacttcctt gcaactcata cctactaaca aactgtttac tcttttttaag    900
gagttagctg cattccctg cggaggtacg tacgcaatca agcagcagg gcagcttcgc       960
aacacctgct tcaacttcat gcacattagc aacaagattg ggtagttgat tgttgggagg   1020
atagctgcag ctccctacgg gagtgaacta cagttccagg gggagcacag caagggccaa   1080
taccggctgt gaggcgcgta gcgggaagag atgtatggta agggatagct gtttaaccat   1140
ttgtaatgga atgggatgtt gatcctcctt ggaataatac gtatataaga agattttcat   1200
tccagttgga aagcaatcga gaaaacgccg cccaaatacg gttcgccacg tgtagccctg   1260
tatggactcg cgaagcaggt ctccggtcgg tgtccaagat ttgatctaac tattgagtga   1320
ggactactta ccgattgata gaataatacg tatataagaa gaaggctgct ttgtggagtg   1380
atctttctcg aaatgaatta agtaagggcg ctatgttcag attctgaacc aaagcactag   1440
ttgaggtctg aaagccttat gagcagaagt aataaatacc tcggggaaga agcgggtag    1500
aggaattggt caactcatca ggctcatgac ctgaagatta caggttcaaa tcctgtcccc   1560
gcaccgtagt ttcattctgc atcactctcc ctgtcgttat cgacctcgca aggttttga    1620
aacggccgaa acgggaagtg acaataccgc ttttcttcag catataaatg caatgattac   1680
cttttcgaa aaattgtcca cttttgtca taatctcact cctactgaat gtaaagttag    1740
tgtaataagt ttctttcttt tagcttttt actaatggcc catatttggc taagctggtt   1800
ttctaacaac caacattgtt tacgaaccat gagacatcta gagaagttaa aaattccata   1860
tgaatttcag tatgggtggc taggtgtcaa aattacaata aaatcaaatg tacctaacga   1920
tgaagtgacg aaaaaagtct cacctatcat taaggggaa atagagggga aagaggaaaa    1980
aaaagagggg aaagggggaaa tagagggaa agaggaaaaa aagaggggga aaggggaaat   2040
agagggaaa gaggaaaaaa aagaggtgga aaatggaccg agaaaataat gctttgtgaa   2100
cccaattgct ttgacaaaaa taagaaaga agcaaaatct cattcaattt gaaatagaag   2160
agatctctat gccccctgtt cttggttttc tcccatgctt tgttggtca acaaccaacc   2220
acaactttct atagttcttc actactccta gaggctttgg taatgaagct gtctggaggg   2280
```

```
atttgttgaa atcaattaat ctaatcatgc ctcaactgga taaattcact tatttttcac    2340
aattcttctg gttatgcctt ttcttcttta ctttctatat tttcatatgc aatgatggag    2400
atggagtact tgggatcagc agaattctaa aactacggaa ccaactgctt tcacaccggg    2460
ggaagaccat ccagagcaag gacccccaaca gtttggaaga tctcttgaga aaaggtttta    2520
gcactggtgt atcctatatg tatgctagtt tattcgaagt atcccaatgg tgtaaggccg    2580
tcgacttatt gggaaaaagg aggaaaatca ctttgatctc ttgtttcgga gaaataagtg    2640
gctcacgagg aatggaaaga aacatattat ataatctatc gaagtcctct ccttcaaata    2700
ctggaaggtg gatcacttgt aggaattgta ggaatgacat aatgctaatc catgctgtac    2760
atggccaagg aagcataaaa tgattctttc attctataga tacctctggt aggtaaagca    2820
ctctactgtg ctttattgaa agttcccatc gcggggcag ggatacttgc cttcgcggtt    2880
cgactttctt ttcaggcttg actcattatt ttccggtcct ctcacacccc tttagagctc    2940
tttatgatgc ccactgagta agattcgggg gcttaccggc gcagaagctc attctgaacc    3000
gcgggaacct tcgtctcttc gacacaaacg ttttatgaag aggctgatgg tgatgaggat    3060
ccatgcgcac tcaaataaaa gtagcttgcg tattgggtta tccacggtgt taggtgctcc    3120
attgcacctc atgtggaggt aggataattt ggactctttt ggagcactat actccgaaag    3180
atcctatcct tcctcctctt ctttcagtcg agacttcctc ctagtgaggt gttgcctatc    3240
caggtatgga agtattcaat gaatacactc tgtaccatgg gtggatgaag ctt           3293

<210> SEQ ID NO 2
<211> LENGTH: 45
<212> TYPE: DNA
<213> ORGANISM: Artificial
<220> FEATURE:
<223> OTHER INFORMATION: Feature : primer (Amorce MF1_M13F)

<400> SEQUENCE: 2
cacgacgttg taaaacgact caattgcaca ttctagaatt ctaag                    45

<210> SEQ ID NO 3
<211> LENGTH: 26
<212> TYPE: DNA
<213> ORGANISM: Artificial
<220> FEATURE:
<223> OTHER INFORMATION: Feature : primer (Amorce MF1_R)

<400> SEQUENCE: 3
caattcaata tggttatata ttagag                                         26

<210> SEQ ID NO 4
<211> LENGTH: 39
<212> TYPE: DNA
<213> ORGANISM: Artificial
<220> FEATURE:
<223> OTHER INFORMATION: Feature : primer (Amorce MF2_M13F)

<400> SEQUENCE: 4
cacgacgttg taaaacgacg gttccgtcgt tcccatcgc                            39

<210> SEQ ID NO 5
<211> LENGTH: 25
<212> TYPE: DNA
<213> ORGANISM: Artificial
<220> FEATURE:
<223> OTHER INFORMATION: Feature : primer (Amorce MF2_R)
```

<400> SEQUENCE: 5
cataataatt agataaatct gttcc    25

<210> SEQ ID NO 6
<211> LENGTH: 42
<212> TYPE: DNA
<213> ORGANISM: Artificial
<220> FEATURE:
<223> OTHER INFORMATION: Feature : primer (Amorce MF3_M13F)

<400> SEQUENCE: 6
cacgacgttg taaaacgaca atggtatgac tagcttataa gg    42

<210> SEQ ID NO 7
<211> LENGTH: 23
<212> TYPE: DNA
<213> ORGANISM: Artificial
<220> FEATURE:
<223> OTHER INFORMATION: Feature : primer (Amorce MF3_R)

<400> SEQUENCE: 7
cttaacaatg agatgaggca atc    23

<210> SEQ ID NO 8
<211> LENGTH: 40
<212> TYPE: DNA
<213> ORGANISM: Artificial
<220> FEATURE:
<223> OTHER INFORMATION: Feature : primer (Amorce MF4_M13F)

<400> SEQUENCE: 8
cacgacgttg taaaacgacc ggatctatta tgacatatcc    40

<210> SEQ ID NO 9
<211> LENGTH: 24
<212> TYPE: DNA
<213> ORGANISM: Artificial
<220> FEATURE:
<223> OTHER INFORMATION: Feature : primer (Amorce MF4_R)

<400> SEQUENCE: 9
gaaatatgaa tacactagat tagg    24

<210> SEQ ID NO 10
<211> LENGTH: 42
<212> TYPE: DNA
<213> ORGANISM: Artificial
<220> FEATURE:
<223> OTHER INFORMATION: Feature : primer (Amorce MF5_M13F)

<400> SEQUENCE: 10
cacgacgttg taaaacgacc ctggcggtat caagatgcca ct    42

<210> SEQ ID NO 11
<211> LENGTH: 21
<212> TYPE: DNA
<213> ORGANISM: Artificial
<220> FEATURE:
<223> OTHER INFORMATION: Feature : primer (Amorce MF5_R)

<400> SEQUENCE: 11
gccataatgg tacagaacta t    21

<210> SEQ ID NO 12
<211> LENGTH: 40

-continued

<210> SEQ ID NO 12
<211> LENGTH: 40
<212> TYPE: DNA
<213> ORGANISM: Artificial
<220> FEATURE:
<223> OTHER INFORMATION: Feature : primer (Amorce MF6_M13F)

<400> SEQUENCE: 12
cacgacgttg taaaacgacg aaggaatagt cgttttcaag          40

<210> SEQ ID NO 13
<211> LENGTH: 22
<212> TYPE: DNA
<213> ORGANISM: Artificial
<220> FEATURE:
<223> OTHER INFORMATION: Feature : primer (Amorce MF6_R)

<400> SEQUENCE: 13
cataattaga gttccatttc gg          22

<210> SEQ ID NO 14
<211> LENGTH: 41
<212> TYPE: DNA
<213> ORGANISM: Artificial
<220> FEATURE:
<223> OTHER INFORMATION: Feature : primer (Amorce MF7_M13F)

<400> SEQUENCE: 14
cacgacgttg taaaacgacc ggcaggagtc attggttcaa a          41

<210> SEQ ID NO 15
<211> LENGTH: 20
<212> TYPE: DNA
<213> ORGANISM: Artificial
<220> FEATURE:
<223> OTHER INFORMATION: Feature : primer (Amorce MF7_R)

<400> SEQUENCE: 15
gattttgtaa ctagctgacg          20

<210> SEQ ID NO 16
<211> LENGTH: 41
<212> TYPE: DNA
<213> ORGANISM: Artificial
<220> FEATURE:
<223> OTHER INFORMATION: Feature : primer (Amorce MF8_M13F)

<400> SEQUENCE: 16
cacgacgttg taaaacgacc ttatattcat aagcgaagaa c          41

<210> SEQ ID NO 17
<211> LENGTH: 22
<212> TYPE: DNA
<213> ORGANISM: Artificial
<220> FEATURE:
<223> OTHER INFORMATION: Feature : primer (Amorce MF8_R)

<400> SEQUENCE: 17
aataacaata gatgaatagt ca          22

<210> SEQ ID NO 18
<211> LENGTH: 39
<212> TYPE: DNA
<213> ORGANISM: Artificial
<220> FEATURE:
<223> OTHER INFORMATION: Feature : primer (Amorce MF9_M13F)

<400> SEQUENCE: 18

```
cacgacgttg taaaacgacg ggccgttatg ctcattacg                                39
```

<210> SEQ ID NO 19
<211> LENGTH: 20
<212> TYPE: DNA
<213> ORGANISM: Artificial
<220> FEATURE:
<223> OTHER INFORMATION: Feature : primer (Amorce MF9_R)

<400> SEQUENCE: 19

```
tcctattcat ggggattccg                                                     20
```

<210> SEQ ID NO 20
<211> LENGTH: 512
<212> TYPE: DNA
<213> ORGANISM: Diplotaxis tenuifolia

<400> SEQUENCE: 20

```
gcatcactct ccctgtcgtt atcgacctcg caaggttttt gagacggccg aaacgggaag         60
tgacaatacc gcttttcttc agcatataaa tgcaatgatt acctttttcg aaaaattgtc        120
cacttttgt cataatctca ctcctactga atgtaaagtt agtgtaataa gtttctttct         180
tttagctttt ttactaatgg cccatatttg gctaagctgg ttttctaaca accaacattg        240
tttacgaacc atgagacatc tagagaagtt aaaaattcca tatgaatttc agtatgggtg        300
gctaggtgtc aaaattacaa taaaatcaaa tgtacctaac gatgaagtga cgaaaaaagt        360
ctcacctatc attaaagggg aaatagaggg gaaagaggaa aaaaagagg ggaaagggga         420
aatagagggg aaagaggaaa aaaagaggg gaaaggggaa atagagggga aagaggaaaa         480
aaagaggtg gaaatggac cgagaaaata at                                        512
```

<210> SEQ ID NO 21
<211> LENGTH: 401
<212> TYPE: DNA
<213> ORGANISM: Diplotaxis tenuifolia

<400> SEQUENCE: 21

```
acgtgtagcc ctgtatggac tcgcgaagca ggtctccggt cggtgtccaa gatttgatct         60
aactattgag tgaggactac ttaccgattg atagaataat acgtatataa aagaaggct         120
gctttgtgga gtgatctttc tcgaaatgaa ttaagtaagg gcgctatgtt cagattctga        180
accaaagcac tagttgaggt ctgaaagcct tatgagcaga agtaataaat acctcgggga        240
agaagcgggg tagaggaatt ggtcaactca tcaggctcat gacctgaaga ttacaggttc        300
aaatcctgtc cccgcaccgt agtttcattc tgcatcactc tccctgtcgt tatcgacctc        360
gcaaggtttt tgaaacggcc gaaacgggaa gtgacaatac c                            401
```

<210> SEQ ID NO 22
<211> LENGTH: 24
<212> TYPE: DNA
<213> ORGANISM: Artificial
<220> FEATURE:
<223> OTHER INFORMATION: Primer (Amorce Oligo 37)

<400> SEQUENCE: 22

```
gcatcactct ccctgtcgtt atcg                                                24
```

<210> SEQ ID NO 23
<211> LENGTH: 24
<212> TYPE: DNA
<213> ORGANISM: Artificial

```
<220> FEATURE:
<223> OTHER INFORMATION: Primer (Amorce Oligo 38)

<400> SEQUENCE: 23
attattttct cggtccattt tcca                                        24

<210> SEQ ID NO 24
<211> LENGTH: 21
<212> TYPE: DNA
<213> ORGANISM: Artificial
<220> FEATURE:
<223> OTHER INFORMATION: Primer (Amorce TRNAFM-610U)

<400> SEQUENCE: 24
acgtgtagcc ctgtatggac t                                           21

<210> SEQ ID NO 25
<211> LENGTH: 21
<212> TYPE: DNA
<213> ORGANISM: Artificial
<220> FEATURE:
<223> OTHER INFORMATION: Primer (Amorce TRNAFM-987L)

<400> SEQUENCE: 25
ggtattgtca cttcccgttt c                                           21

<210> SEQ ID NO 26
<211> LENGTH: 21
<212> TYPE: DNA
<213> ORGANISM: Artificial
<220> FEATURE:
<223> OTHER INFORMATION: Primer (Amorce COX1-244U)

<400> SEQUENCE: 26
ggtaattggt ttgttccgat t                                           21

<210> SEQ ID NO 27
<211> LENGTH: 21
<212> TYPE: DNA
<213> ORGANISM: Artificial
<220> FEATURE:
<223> OTHER INFORMATION: Primer (Amorce COX1-805L)

<400> SEQUENCE: 27
catgcctaga tacccgaaga c                                           21
```